United States Patent
Jeong et al.

(10) Patent No.: US 9,452,159 B2
(45) Date of Patent: Sep. 27, 2016

(54) 6-AMINOPYRIDINE-3-OL DERIVATIVES OR PHARMACEUTICALLY ACCEPTABLE SALTS THEREOF, AND PHARMACEUTICAL COMPOSITION CONTAINING SAME AS ACTIVE INGREDIENTS FOR PREVENTING OR TREATING DISEASES CAUSED BY ANGIOGENESIS

(71) Applicant: Research Cooperation Foundation of Yeungnam University, Gyeongsan-si, Gyeongsangbuk-do (KR)

(72) Inventors: Byeong Seon Jeong, Daegu (KR); Jung Ae Kim, Daegu (JP); Dong Guk Kim, Daegu (JP); You Ra Kang, Gyeongsan-si (KR); Tae Gyu Nam, Suwon-si (KR)

(73) Assignee: RESEARCH COOPERATION OF YEUNGNAM UNIVERSITY, Gyeongsan-Si, Gyeongsangbuk-Do (KR)

( * ) Notice: Subject to any disclaimer, the term of this patent is extended or adjusted under 35 U.S.C. 154(b) by 0 days.

(21) Appl. No.: 14/367,237

(22) PCT Filed: Dec. 21, 2012

(86) PCT No.: PCT/KR2012/011302
§ 371 (c)(1),
(2) Date: Jun. 20, 2014

(87) PCT Pub. No.: WO2013/095060
PCT Pub. Date: Jun. 27, 2013

(65) Prior Publication Data
US 2015/0238471 A1    Aug. 27, 2015

(30) Foreign Application Priority Data

Dec. 21, 2011 (KR) ......... 10-2011-0139306
Dec. 20, 2012 (KR) ......... 10-2012-0149669

(51) Int. Cl.
*A61P 25/00* (2006.01)
*A61K 31/4402* (2006.01)
(Continued)

(52) U.S. Cl.
CPC ............ *A61K 31/44* (2013.01); *A61K 31/444* (2013.01); *A61K 31/4433* (2013.01); *A61K 31/4439* (2013.01); *A61K 31/496* (2013.01); *A61K 31/5377* (2013.01); *C07D 213/74* (2013.01)

(58) Field of Classification Search
CPC ... A61P 25/00; A61P 29/00; A61K 31/4402; C07D 213/74
USPC ....................................... 514/235.5
See application file for complete search history.

(56) References Cited

U.S. PATENT DOCUMENTS

2008/0227776 A1    9/2008 Oates et al.
2015/0031890 A1 *  1/2015 Jeong ................ A61K 31/4745
                                                546/122
(Continued)

FOREIGN PATENT DOCUMENTS

JP    2011032210    *  2/2011
WO   2004-004720 A1    1/2004
WO   2010-086646 A1    8/2010

OTHER PUBLICATIONS

De Angelis; Bioorganic & Medicinal Chemistry Letters 14 (2004) 5835-5839.*
Nam; Org. Biomol. Chem., 2009, 7, 5103-5112.*
Serwa; Chem. Eur. J. 2010, 16, 14106-14114.*
Simone, Oncology: Introduction, Cecil Textbook of Medicine, 20th Edition, 1996 vol. 1, pp. 1004-1010.*

(Continued)

*Primary Examiner* — Andrew D Kosar
*Assistant Examiner* — Daniel Carcanague
(74) *Attorney, Agent, or Firm* — Revolution IP, PLLC

(57) ABSTRACT

A method or composition including 6-aminopyridin-3-ol derivatives or pharmaceutically acceptable salts thereof for treating a disease caused by angiogenesis, the 6-aminopyridin-3-ol derivatives represented by Formula 1 or the pharmaceutically acceptable salts thereof have excellent neoangiogenesis inhibition effects in the chorioallantoic membrane model, and are suitable for use as a drug for the treatment of disease caused by angiogenesis.

5 Claims, 5 Drawing Sheets

(51) Int. Cl.
*C07D 213/74* (2006.01)
*A61P 29/00* (2006.01)
*A61K 31/44* (2006.01)
*A61K 31/4433* (2006.01)
*A61K 31/4439* (2006.01)
*A61K 31/444* (2006.01)
*A61K 31/496* (2006.01)
*A61K 31/5377* (2006.01)

(56) References Cited

U.S. PATENT DOCUMENTS

2015/0320729 A1* 11/2015 Jeong ............... A61K 31/4745 514/300
2016/0068489 A1* 3/2016 Jeong ............... A61K 31/4402 514/338

OTHER PUBLICATIONS

Johnson; British Journal of Cancer 2001, 84, 1424-1431.*
Ribatti; Pharmaceuticals 2010, 3, 482-513.*
Omata; Free Radical Biology & Medicine 2010, 48, 1358-1365.*
Arce; Bioorganic & Medicinal Chemistry 2012, 20, 5188-5201.*
Kim; European Journal of Medicinal Chemistry 2014, 78, 126-139.*
PubChemCompound, datasheet [online compound summary] Retrieved from the Internet: <URL: http://pubchem.ncbi.nlm.nih.gov/search/search.cgi> CID 23292067, CID 17819954, CID 23145495, CID 23145410, CID 23145727 etc., Dated Dec. 2007.
A.A.Sologub et al., "Emoxypine as an inhibitor of angiogenesis", Bulletin of Experimental Biology and Medicine, 1992, vol. 114, No. 6, pp. 1827-1830.

* cited by examiner

| Treatment | | Angiogenesis inhibition (%) | Tumor growth inhibition (%) |
|---|---|---|---|
| | PBS | | |
| | 0.0001 | 12.9 ± 5.6 | 14.8 ± 4.2 |
| 6a (μM) | 0.001 | 16.6 ± 3.2 | 20.5 ± 5.1 |
| | 0.01 | 18.0 ± 7.8 | 25.2 ± 8.0 |
| | 0.1 | 20.7 ± 3.6 | 27.4 ± 7.8 |
| A549 | PBS | | |
| | 0.0001 | 18.3 ± 5.1 | 21.0 ± 8.7 |
| 6i (μM) | 0.001 | 19.9 ± 1.9 | 25.3 ± 5.7 |
| | 0.01 | 25.6 ± 4.5 | 44.4 ± 6.0 |
| | 0.1 | 34.5 ± 2.8 | 50.1 ± 5.6 |

6-AMINOPYRIDINE-3-OL DERIVATIVES OR PHARMACEUTICALLY ACCEPTABLE SALTS THEREOF, AND PHARMACEUTICAL COMPOSITION CONTAINING SAME AS ACTIVE INGREDIENTS FOR PREVENTING OR TREATING DISEASES CAUSED BY ANGIOGENESIS

CROSS REFERENCE TO PRIOR APPLICATIONS

This application is the 35 U.S.C. 371 national stage of International application PCT/KR2012/011302 filed on Dec. 21, 2012; which claims priority to Korean applications 10-2011-0139306 and 10-2012-0149669 filed on Dec. 21, 2011 and Dec. 20, 2012, respectively.

TECHNICAL FIELD

The present invention relates to 6-aminopyridin-3-ol derivatives or pharmaceutically acceptable salts thereof and pharmaceutical compositions for the prevention or treatment of disease caused by angiogenesis containing disease caused by angiogenesis including the same as an active ingredient.

PRIOR ART

Angiogenesis is the process through which new capillary vessels form from existing micro vessels. Angiogenesis normally occurs during embryonic development, tissue regeneration, wound healing, and corpus luteum development that is a cyclic change of female reproductive system, and even in these cases, angiogenesis occurs under stringent control (Folkman J et al., Int. Rev. Exp. Pathol., 16, pp 207-248, 1976).

For adults, endothelial cells very slowly grow, and compared to other kinds of cells, they do not divide well. Angiogenesis occurs such that in general, due to the stimulus of a promotion factor for angiogenesis, vascular basal membrane decomposes by protease, and endothelial cells move, proliferate, and differentiate, leading to formation of lumen and reconstruction of vessels, forming new capillary vessels.

However, in some cases, angiogenesis may not be autonomously controlled but pathologically grows to cause disease. Examples of angiogenesis-associated disease that occurs in a pathologic state are hemangioma, angiofibroma, vascular malformation, and cardiovascular disease, such as arteriosclerosis, vascular adhesion, or scleroedema, and examples of angiogenesis-associated ophthalmic disease are keratoplasty angiogenesis, angiogenic glaucoma, diabetic retinopathy, neovascular corneal disease, macular degeneration, pterygium, retinal degeneration, retrolental fibroplasia, and trachoma. Chronic inflammatory disease, such as arthritis, dermatology disease, such as acne, psoriasis, capillarectasia, granuloma pyogenicum, or dermatitis seborrheica, Alzheimer's disease, and obesity are also associated with angiogenesis, and the growth and metastasis of cancer are necessarily dependent on angiogenesis (D'Amato R J et al., Ophthalmology, 102(9), pp 1261-1262, 1995; Arbiser J L, J. Am. Acad. Dermatol., 34(3), pp 486-497, 1996; O'Brien K D et al. Circulation, 93(4), pp 672-682, 1996; Hanahan D et al., Cell, 86, pp 353-364, 1996).

In particular, in the case of cancer, angiogenesis plays a critical role in the growth and metastasis of cancer cells. Tumors are fed with nutrition and oxygen required for the growth and proliferation through new blood vessels, and new blood vessels permeated into tumor allow metastasizing cancer cells to enter a blood circulation system, causing metastasis of cancer cells (Folkman and Tyler, Cancer Invasion and metastasis, Biologic mechanisms and Therapy (S. B. Day ed.) Raven press, New York, pp 94-103, 1977; Polverini P J, Crit. Rev. Oral. Biol. Med., 6(3), pp 230-247, 1995). The major death cause of cancer patients is metastasis, which often leads to the failure of clinical chemotherapy or immuno-therapy performed to increase survival rate of cancer patients.

Arthritis, which is a representative inflammatory disease, is caused by abnormal autoimmune system. However, when the disease progresses, chronic inflammation developed in synovial cavity between joints induces angiogenesis and destroys cartilage. That is, cytokines inducing inflammation help proliferation of synovial cells and vascular endothelial cells in synovial cavity, and while angiogenesis progresses, joint pannus, which is a connective tissue occurring in a cartilage site, is formed to destroy cartilage acting as a cushion (Koch A E et al., Arthritis. Rheum., 29, pp 471-479, 1986; Stupack D G et al., Braz J. Med. Biol. Rcs., 32(5), pp 578-581, 1999; Koch A E, Arthritis. Rheum., 41(6), pp 951-962, 1998).

Each year, many ophthalmic diseases cause blindness in hundreds of people worldwide, and induce angiogenesis (Jeffrey M I et al., J. Clin. Invest., 103, pp 1231-1236, 1999). Representative examples of such diseases are macular degeneration, which occurs in old people, diabetic retinopathy, premature infant retinopathy, neovascular glaucoma, and corneal disease caused by neovascularization cause angiogenesis (Adamis A P et al., Angiogenesis, 3, pp 9-14, 1999). From among these disease, diabetic retinopathy is a complication of diabetes that causes blindness by invasiveness of retinal capillary vessels into hyaloid.

Psoriasis characterized with red spots and scaly skin is also a chronic proliferative disease that develops in the skin. Psoriasis is not treatable and accompanies pains and malformation. In a normal case, horny cells proliferate once a month. However, in the case of psoriasis patients, horny cells proliferate at least once a week. This rapid proliferation needs much blood, which is why angiogenesis actively occurs (Folkman J, J. Invest. Dermatol., 59, pp 40-48, 1972).

Angiogenesis inhibitors can be used as a therapeutic agent for these angiogenesis-associated diseases. Accordingly, research into how to treat these diseases by inhibiting angiogenesis is actively being performed. In general, angiogenesis inhibitors are administered to patients for a long period of time, so that they desirably need to be non-toxic and orally administrable. Accordingly, there is a need to develop as an angiogenesis inhibitor a drug whose toxicity is negligible.

DETAILED DESCRIPTION OF THE INVENTION

Technical Field

In response, the inventors of the present application confirmed that 6-aminopyridin-3-ol derivatives each having a particular structure or pharmaceutically acceptable salts thereof has excellent angiogenesis inhibiting effects, thereby completing the present invention.

Accordingly, the purpose of the present invention is to provide pharmaceutical compositions for the prevention or treatment of disease caused by angiogenesis including 6-aminopyridin-3-ol derivatives or pharmaceutically acceptable salts thereof as an active ingredient.

Technical Solution

The present invention provides a 6-aminopyridin-3-ol derivative represented by Formula 1 below or a pharmaceutically acceptable salt thereof:

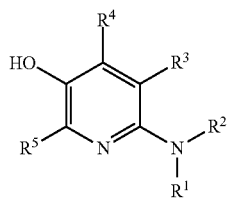

[Formula 1]

wherein
$R^1$ is a hydrogen, a C1 to C4 alkyl, or a phenyl, $R^2$ is a C1 to C16 hydroxyalkyl, a C2 to C4 (5-hydroxy-trimethylpyridin-2-yl)alkoxy, a C3 to C7 cycloalkyl, benzyl, a phenyl, a C1 to C4 alkylphenyl, a nitrophenyl, a halophenyl, a benzo[d][1,3]-dioxol-5-yl, or a pyridine-2-yl; or $R^1$ and $R^2$ are linked to each other to form a 5-membered ring or a 6-membered ring, thereby forming a heterocyclic compound, and $R^3$ to $R^5$ are identical or different, and are each a hydrogen or a C1 to C4 alkyl.

Also, the present invention provides pharmaceutical compositions for the prevention or treatment of disease caused by angiogenesis including 6-aminopyridin-3-ol derivatives represented by Formula 1 or pharmaceutically acceptable salts thereof as an active ingredient.

Advantageous Effects 6-aminopyridin-3-ol derivatives or pharmaceutically acceptable salts thereof according to the present invention inhibit an increase in angiogenesis caused by treatment with a angiogenesis-inducing material, such as a vascular endothelial growth factor, in chick chorioallantoic membrane model, and accordingly, they may be suitable for use as a drug for the prevention or treatment of disease caused by angiogenesis.

BEST MODE

Figure 1:
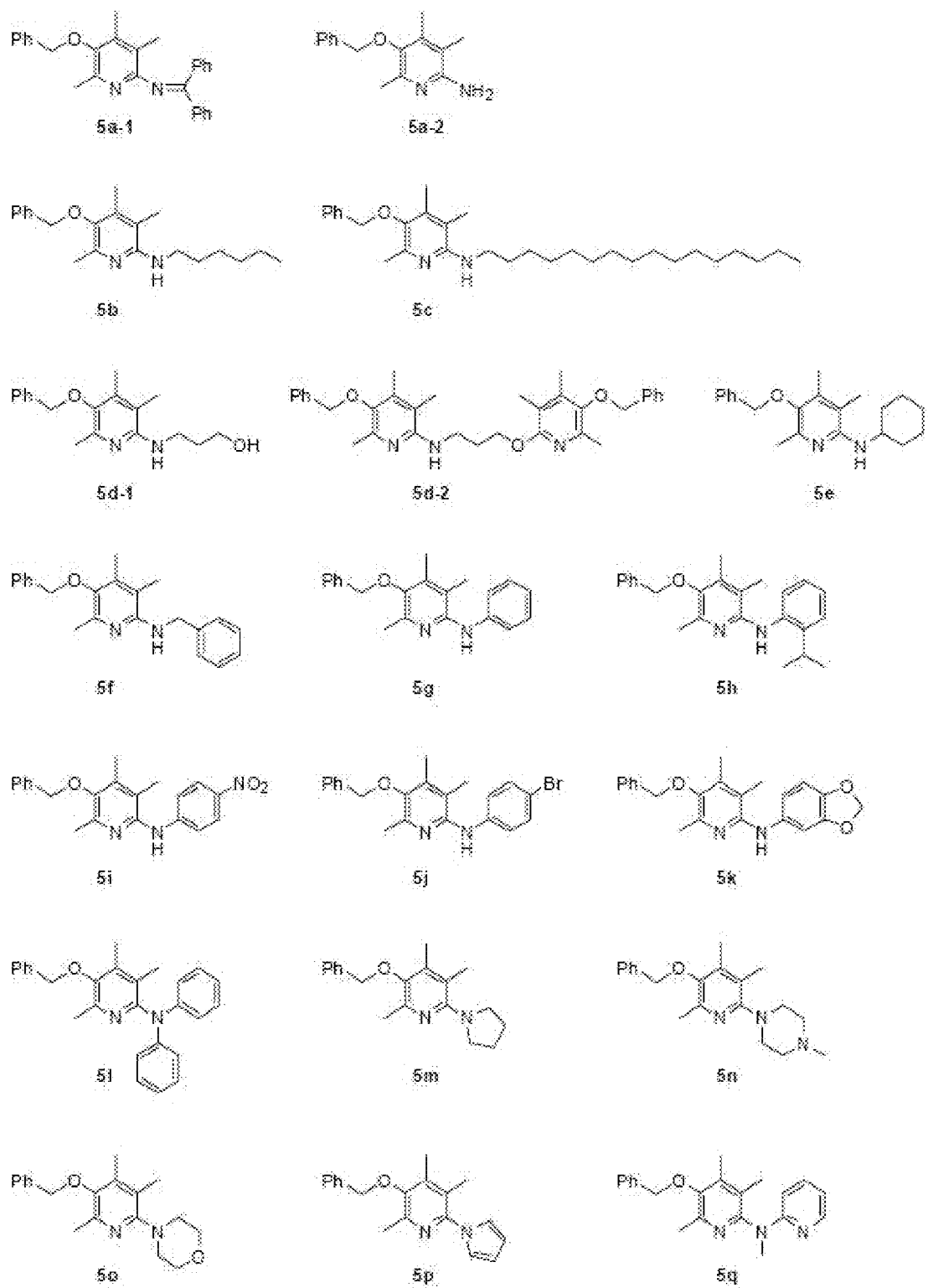
FIG. 1 shows formulae of intermediate compounds used to prepare a 6-aminopyridin-3-ol derivative or a pharmaceutically acceptable salt thereof according to an embodiment of the present invention.
Figure 2:
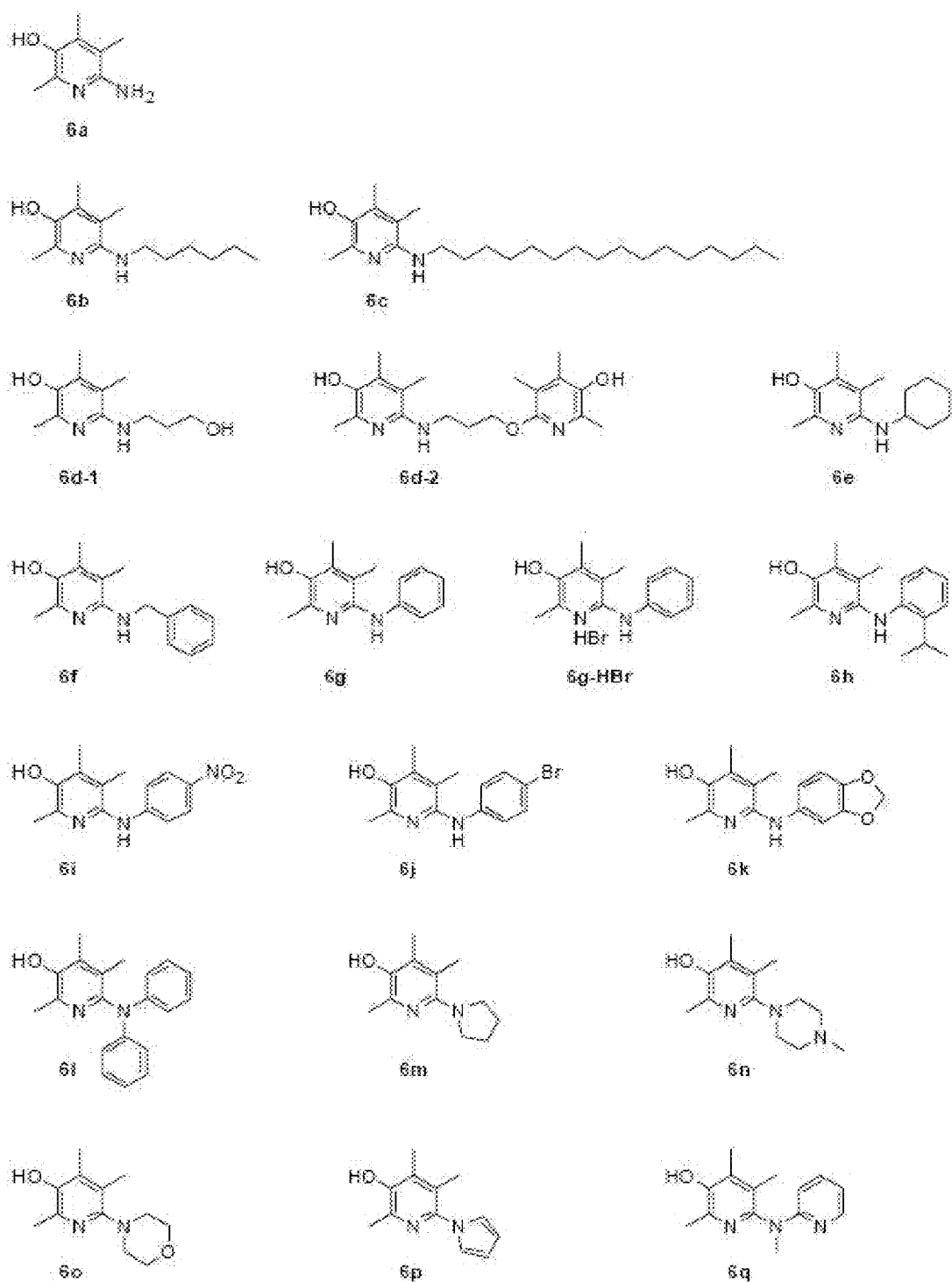
FIG. 2 shows formulae of 6-aminopyridin-3-ol derivatives or pharmaceutically acceptable salts thereof according to an embodiment of the present invention.

The present invention provides a 6-aminopyridin-3-ol derivative represented by Formula 1 below or a pharmaceutically acceptable salt thereof:

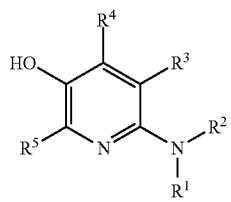

[Formula 1]

wherein
$R^1$ may be a hydrogen, a C1 to C4 alkyl, or a phenyl, $R^2$ may be a C1 to C16 hydroxyalkyl, a C2 to C4 (5-hydroxy-trimethylpyridin-2-yl)alkoxy, a C3 to C7 cycloalkyl, benzyl, a phenyl, a C1 to C4 alkylphenyl, a nitrophenyl, a halophenyl, a benzo[d][1,3]-dioxol-5-yl, or a pyridine-2-yl; or $R^1$ and $R^2$ may be linked to each other to form a 5-membered ring or a 6-membered ring, thereby forming a heterocyclic compound, and $R^3$ to $R^5$ may be identical or different, and may be a hydrogen or a C1 to C4 alkyl.

In some embodiments, in the formula representing the derivative, $R^1$ may be a hydrogen, a C1 to C4 alkyl, or a phenyl, $R^2$ may be a C1 to C6 hydroxyalkyl, (5-hydroxy-3,4,6-trimethylpyridin-2-yl)propoxy, a C5 to C6 cycloalkyl, a benzyl, a phenyl, a C1 to C4 alkylphenyl, a nitrophenyl, a halophenyl, or a benzo[d][1,3]-dioxol-5-yl or pyridine-2-yl; or $R^1$ and $R^2$ are linked to each other to form a 5-membered ring to a 6-membered ring, thereby forming a heterocyclic compound, and may be pyrrolidine-1-yl, 4-methylpiperazine-1-yl, 6-morpholinos, or 1H-pyrrol-1-yl, and $R^3$ to $R^5$ are all a methyl.

The pharmaceutically acceptable salt may be an acid-added salt formed from either an organic acid selected from the group consisting of an oxalic acid, a maleic acid, a fumaric acid, a malic acid, a tartaric acid, a citric acid, and a benzoic acid, or an inorganic acid selected from the group consisting of a hydrochloric acid, a sulfuric acid, a phosphoric acid, and a hydrobromic acid.

In some embodiments, the derivative or pharmaceutically acceptable salt thereof may be selected from 6-((3-hydroxypropyl)amino)-2,4,5-trimethylpyridin-3-ol; 6-(3-((5-hydroxy-3,4,6-trimethylpyridin-2-yl)amino)propoxy)-2,4,5-trimethyl pyrid in-3-ol; 6-(cyclohexylamino)-2,4,5-trimethylpyridin-3-ol; 6-(benzylamino)-2,4,5-trimethylpyridin-3-ol; 2,4,5-trimethyl-6-(phenylamino) pyridin-3-ol; 6-((2-isopropylphenyl)amino)-2,4,5-trimethylpyridin-3-ol; 2,4,5-trimethyl-6-((4-nitrophenyl)amino)pyridin-3-ol; 6-((4-bromophenyl)amino)-2,4,5-trimethylpyridin-3-ol; 2,4,5-trimethyl-6-(phenylamino) pyridin-3-ol hydrobromide; 6-(benzo[d][1,3]dioxol-5-ylamino)-2,4,5-trimethylpyridin-3-ol; 6-(diphenylamino)-2,4,5-trimethylpyridin-3-ol; 2,4,5-trimethyl-6-(pyrrolidin-1-yl)pyridin-3-ol; 2,4,5-trimethyl-6-(4-methylpiperazin-1-yl) pyridin-3-ol; 2,4,5-trimethyl-6-morpholinospyridin-3-ol;

2,4,5-trimethyl-6-(1H-pyrrol-1-yl)pyridin-3-ol; and 2,4,5-trimethyl-6-(methyl(pyridin-2-yl)amino)pyridin-3-ol.

The 6-aminopyridin-3-ol derivative represented by Formula 1 or pharmaceutically acceptable salt thereof according to the present invention may be prepared according to a preparation method shown in Reaction Scheme 1 below:

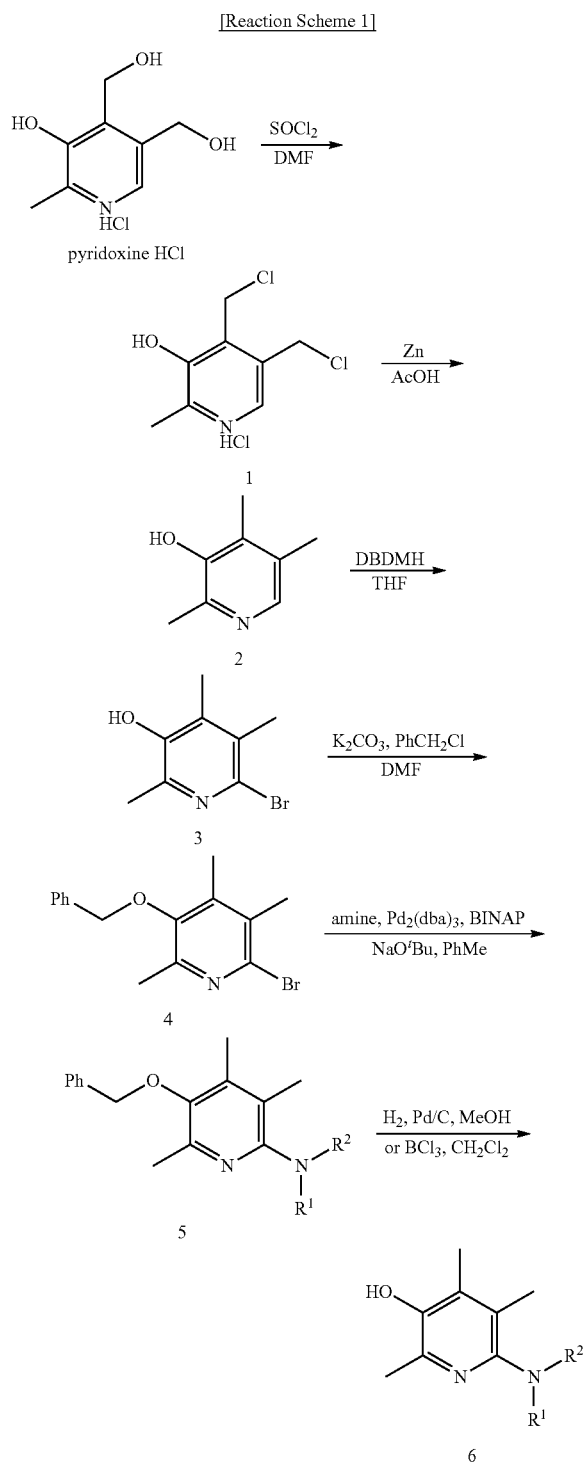

In detail, SOCl$_2$ and dimethylformamide (DMF) are added to pyridoxine hydrochloride and then the mixture is refluxed while stirring to obtain Compound 1. Then, zinc powder is added in a small amount to a reaction solution prepared by suspending Compound 1 in an acetic acid, and the result is refluxed while stirring to obtain Compound 2. Then, 1,3-dibromo-5,5-dimethylhidantoin (DBDMH) is added to a reaction solution prepared by suspending Compound 2 in tetrahydrofuran (THF), and the result is stirred to obtain Compound 3. Then, K$_2$CO$_3$ and benzyl chloride (PhCH$_2$Cl) are added to a reaction solution prepared by dissolving Compound 3 in DMF, and the result is stirred to obtain Compound 4. Then, an amine compound is added to a reaction solution prepared by dissolving Compound 4, NaOtBu, tri(dibenzyllidene acetone)dipalladium (Pd$_2$(dba)$_3$), and 2,2'-bis(diphenylphosphino)-1,1'-binaphthyl(BINAP) in toluene, and then, the result is refluxed while stirring to obtain Compound 5. Then, Pd/C is added to a reaction solution prepared by dissolving Compound 5 in methanol, and the result is stirred under a hydrogen stream to obtain Compound 6. Alternatively, BCl$_3$ may be added to a reaction solution prepared by dissolving Compound 5 in CH$_2$Cl$_2$ to obtain Compound 6.

Also, the present invention provides pharmaceutical compositions for the prevention or treatment of disease caused by angiogenesis including 6-aminopyridin-3-ol derivatives represented by Formula 1 below or pharmaceutically acceptable salts thereof as an active ingredient:

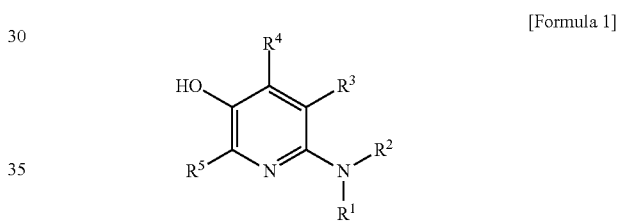

[Formula 1]

wherein $R^1$ may be a hydrogen, a C1 to C4 alkyl, or a phenyl, $R^2$ may be a hydrogen, a C1 to C16 alkyl, a C1 to C16 hydroxyalkyl, a C2 to C4 (5-hydroxy-trimethylpyridin-2-yl) alkoxy, a C3 to C7 cycloalkyl, benzyl, a phenyl, a C1 to C4 alkylphenyl, a nitrophenyl, a halophenyl, a benzo[d][1,3]-dioxol-5-yl, or a pyridine-2-yl; or $R^1$ and $R^2$ may be linked to each other to form a 5-membered ring or a 6-membered ring, thereby forming a heterocyclic compound, and may be any one selected from pyrrolidine-1-yl, 4-methylpiperazine-1-yl, 6-morpholinos, and 1H-pyrrol-1-yl, and $R^3$ to $R^5$ may be identical or different, and may be a hydrogen or a C1 to C4 alkyl.

In some embodiments, in the formula representing the derivative, $R^1$ may be a hydrogen, a C1 to C4 alkyl, or a phenyl, $R^2$ may be a hydrogen, a C6 to C16 alkyl, a C1 to C6 hydroxyalkyl, (5-hydroxy-3,4,6-trimethylpyridin-2-yl) propoxy, a C5 to C6 cycloalkyl, a benzyl, a phenyl, a C1 to C4 alkylphenyl, a nitrophenyl, a halophenyl, or a benzo[d][1,3]-dioxol-5-yl or pyridine-2-yl; or $R^1$ and $R^2$ are linked to each other to form a 5-membered ring to a 6-membered ring, thereby forming a heterocyclic compound, and may be pyrrolidine-1-yl, 4-methylpiperazine-1-yl, 6-morpholinos, or 1H-pyrrol-1-yl, and $R^3$ to $R^5$ are all a methyl.

The pharmaceutically acceptable salt may be an acid-added salt formed from either an organic acid selected from the group consisting of an oxalic acid, a maleic acid, a fumaric acid, a malic acid, a tartaric acid, a citric acid, and a benzoic acid, or an inorganic acid selected from the group consisting of a hydrochloric acid, a sulfuric acid, a phosphoric acid, and a hydrobromic acid.

In detail, the derivative or pharmaceutically acceptable salt thereof may be selected from 6-amino-2,4,5-trimethylpyridin-3-ol; 6-(hexylamino)-2,4,5-trimethylpyridin-3-ol; 6-(hexadecylamino)-2,4,5-trimethylpyridin-3-ol; 6-((3-hydroxypropyl)amino)-2,4,5-trimethylpyridin-3-ol; 6-(3-((5-hydroxy-3,4,6-trimethylpyridin-2-yl)amino)propoxy)-2,4,5-trimethylpyridin-3-ol; 6-(cyclohexylamino)-2,4,5-trimethylpyridin-3-ol; 6-(benzylamino)-2,4,5-trimethylpyridin-3-ol; 2,4,5-trimethyl-6-(phenylamino)pyridin-3-ol; 6-((2-isopropylphenyl)amino)-2,4,5-trimethylpyridin-3-ol; 2,4,5-trimethyl-6-((4-nitrophenyl)amino)pyridin-3-ol; 6-((4-bromophenyl)amino)-2,4,5-trimethylpyridin-3-ol; 2,4,5-trimethyl-6-(phenylamino)pyridin-3-ol hydrobromide; 6-(benzo[d][1,3]dioxol-5-ylamino)-2,4,5-trimethylpyridin-3-ol; 6-(diphenylamino)-2,4,5-trimethylpyridin-3-ol; 2,4,5-trimethyl-6-(pyrrolidin-1-yl)pyridin-3-ol; 2,4,5-trimethyl-6-(4-methylpiperazin-1-yl)pyridin-3-ol; 2,4,5-trimethyl-6-morpholinospyridin-3-ol; 2,4,5-trimethyl-6-(1H-pyrrol-1-yl)pyridin-3-ol; and 2,4,5-trimethyl-6-(methyl(pyridin-2-yl)amino)pyridin-3-ol.

The disease caused by angiogenesis may be any one selected from the group consisting of rheumatoid arthritis, osteoarthritis, septic arthritis, psoriasis, corneal ulcers, age-related macular degeneration, diabetic retinopathy, proliferative vitreoretinopathy, retinopathy of prematurity, ophthalmic inflammation, keratoconus, Sjogren syndrome, myopia ophthalmic tumors, corneal graft rejection, abnormal wound fusion, bone disease, albuminuria, abdominal aorta disease, degenerative cartilage loss due to traumatic joint injuries, myelinoclasis diseases of the nervous system, cirrhosis, glomerular diseases, premature rupture of the embryonic membrane, inflammatory bowel disease, periodontal disease, atherosclerosis, re-stenosis, inflammatory disease of the central nervous system, Alzheimer's disease, skin aging, and the invasion and metastasis of cancer.

6-aminopyridin-3-ol derivatives or pharmaceutically acceptable salts thereof according to the present invention inhibit an increase in angiogenesis caused by treatment with a angiogenesis-inducing material, such as a vascular endothelial growth factor, in chick chorioallantoic membrane model, and accordingly, they may be suitable for use as an active ingredient for the prevention or treatment of disease caused by angiogenesis.

The amount and use method of the pharmaceutical composition may vary according to formulation and purpose.

The pharmaceutical composition according to the present invention may include the 6-aminopyridin-3-ol derivative or pharmaceutically acceptable salt thereof in an amount of 0.1 to 50 wt % based on the total weight of the composition.

In some embodiments, the pharmaceutical composition according to the present invention may further include a carrier, an excipient, and a diluent which are conventionally used in preparing a pharmaceutical composition.

Examples of the carrier, the excipient, and the diluent are lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propylhydroxylbenzoate, talc, magnesium stearate, and mineral oil.

The pharmaceutical composition according to the present invention may be prepared in various formulations according to various conventional methods. For example, the pharmaceutical composition may be prepared in an oral formulation, an external-use formulation, a suppository formulation, or a sterile injection formulation. The oral formulation may be powder, granule, tablet, capsule, suspension, emulsion, syrup, or aerosols.

During preparation, a diluent or an excipient, such as fillers, thickeners, binders, wetting agents, disintegrants, or surfactants, may be used. For use as a solid preparation for oral administration, tablets, pills, powders, granules, capsules and so on are included, and these solid preparations may be prepared by mixing with at least one of the above-mentioned compounds, for example, starch, calcium carbonate, sucrose, or lactose, or gelatin.

In addition to the simple excipient, lubricants, such as magnesium stearate and talc, may also be used herein. A liquid preparation for oral administration may be a suspension, a liquid for internal use, an emulsion, or a syrup, and includes various excipients, such as, for example, a wetting agent, a sweetening agent, an aromatic and a preservative, in addition to simple diluents such as water and liquid paraffin widely used in the art. A preparation for non-oral administration includes a sterile aqueous solution, a non-aqueous solvent, a suspension, an emulsion, a lyophilized preparation, or a suppository. A vegetable oil such as propylene glycol, polyethylene glycol, or olive oil, or an injectable ester such as ethyl oleate may be used as the non-aqueous solvent or suspension. A base of the suppository that may be used herein may include witepsol, macrogol, Tween 61, cacao butter, laurin butter or glycerogelatin.

The dosage of 6-aminopyridin-3-ol derivative or pharmaceutically acceptable salt thereof according to the present invention may vary according to the age, gender, or body weight of a patient, and may be in a range of 0.001 to 100 mg/kg, for example, 0.01 to 10 mg/kg, and these ranges of amount may be administered once a day or may be divided into several portions which are then separately administered within a day. The dosage of 6-aminopyridine-3-ol derivative or pharmaceutically acceptable salt thereof may vary according to administration passage, severity of disease, gender, body weight, age, or the like. Accordingly, the dosage, in any aspects, does not limit the scope of the present invention.

The pharmaceutical composition may be administered to rats, mice, livestock, humans, or the like thorough various administration routes. All of these administration routes are expectable, and for example, the composition may be administered orally, rectally, intravenously, muscularly, subcutaneously, intrauterine-subdurally or intracerebroventricularly.

The 6-aminopyridin-3-ol derivative or pharmaceutically acceptable salt thereof according to the present invention has a 50% lethal amount ($LC_{50}$) of 2 g/kg or more, thereby having safety. Accordingly, the 6-aminopyridine-3-ol derivative or pharmaceutically acceptable salt thereof according to the present invention can be used in a pharmaceutical composition according to the present invention.

EMBODIMENTS

Hereinafter, embodiments of the present invention will be described herein. However, the embodiments do not limit the present invention.

Example 1

Synthesis of 4,5-bis(chloromethyl)-2-methylpyridin-3-ol hydrochloride; 1

$SOCl_2$ (30 mL) and DMF (0.2 mL, 2.583 mmol) were added to pyridoxine.HCl (5 g, 24.31 mmol), and then, the mixture was refluxed while stirring at a temperature of 80° C. for 3 hours. The reaction solution was cooled to room temperature, and then, Et$_2$O (70 mL) was added thereto, and the result was stirred for 1 hour under ice cooling. Precipitated solid was filtered under reduced pressure, and the filtered solid was washed with Et$_2$O and then dried to obtain Compound 1 (5.5 g, 93%) in the form of white solid.

$^1$H-NMR (250 MHz, DMSO-d$_6$) δ 8.42 (s, 1H), 4.99 (s, 2H), 4.96 (s, 2H), 2.63 (s, 3H) ppm.

Example 2

Synthesis of 2,4,5-trimethylpyridin-3-ol; 2

Zinc powder (8.08 g, 123.69 mmol) was separately added in small portions to an acetic acid (50 mL) suspension of Compound 1 (10 g, 41.23 mmol), and then, the mixture was refluxed while stirring at a temperature of 130° C. for 2 hours. The reaction solution was cooled to room temperature, and then filtered under reduced pressure, and a pH of the residual was controlled to be 6 by using a 10 M NaOH solution. Then, the residual was saturated with salt and extracted with EtOAc (100 mL×6). The EtOAc solution was washed with the saturated saline water, followed by drying with MgSO$_4$, filtering, and concentrating under reduced pressure. The residual was purified by column chromatography (CHCl$_3$:MeOH=20:1) to obtain Compound 2 (5.2 g, 92%) in the form of white solid.

$^1$H-NMR (250 MHz, DMSO-d$_6$) δ 8.49 (s, 1H), 7.72 (s, 1H), 2.31 (s, 3H), 2.12 (s, 3H), 2.08 (s, 3H) ppm.

Example 3

Synthesis of 6-bromo-2,4,5-trimethylpyridin-3-ol; 3

1,3-dibromo-5,5-dimethylhydantoin (DBDMH, 2.5 g, 9.11 mmol) was added to a THF (30 mL) suspension of Compound 2 (2.5 g, 18.22 mmol), and then, the mixture was stirred at room temperature for 3 hours. The reaction solution was concentrated and then, the residual was diluted with EtOAc (500 mL) and water (20 mL) and a water layer was extracted by using EtOAc (100 mL×3). The EtOAc solution was washed with the saturated saline water, followed by drying with MgSO$_4$, filtering, and concentrating under reduced pressure. The residual was purified by column chromatography (EtOAc:Hex=1:4) to obtain Compound 3 (3.22 g, 80%) in the form of light yellow solid.

$^1$H-NMR (250 MHz, CHCl$_3$-d) δ 5.56 (br s, 1H), 2.42 (s, 3H), 2.31 (s, 3H), 2.25 (s, 3H) ppm.

Example 4

Synthesis of 3-(benzyloxy)-6-bromo-2,4,5-trimethylpyridine; 4

K$_2$CO$_3$ (20.78 g, 150.04 mmol) and benzyl chloride (5.2 mL, 45.12 mmol) were sequentially added to a DMF (15 mL) solution of Compound 3 (6.5 g, 30.08 mmol), and then, the result was stirred at room temperature for 12 hours. The reaction solution was diluted with EtOAc (700 mL) and washed with water (20 mL×10). The EtOAc solution was washed with the saturated saline water, followed by drying with MgSO$_4$, filtering, and concentrating under reduced pressure. The residual was purified by column chromatography (EtOAc:Hex=1:20) to obtain Compound 4 (8.9 g, 97%) in the form of white solid.

$^1$H-NMR (250 MHz, CHCl$_3$-d) δ 7.387.43 (m, 5H), 4.77 (s, 2H), 2.46 (s, 3H), 2.32 (s, 3H), 2.24 (s, 3H) ppm.

Example 5

Synthesis of 5-(benzyloxy)-N-(diphenylmethylene)-3,4,6-trimethylpyridin-2-amine; 5a-1

Benzophenon imine (1.73 mL, 9.80 mmol) was added to a toluene (30 mL) solution of Compound 4 (3 g, 9.80 mmol), NaO$^t$Bu (1.36 g, 13.71 mmol), tri(dibenzyllidene acetone) dipalladium [(Pd$_2$(DBA)$_3$, 203 mg, 0.20 mmol], and 2,2'-bis(diphenylphosphino)-1,1'-binaphthyl (BINAP, 249 mg, 0.39 mmol), and then, the result was refluxed while stirring at a temperature of 120° C. for 12 hours. The reaction solution was cooled to room temperature and then diluted with EtOAc (700 mL) and water (10 mL), and the EtOAc solution was washed with saturated saline water (30 mL×5). The result was dried with MgSO$_4$, filtered, and concentrated under reduced pressure. The residual was purified by column chromatography (EtOAc:Hex=1:4) to obtain Compound 5a-1 (3.28 g, 83%) in the form of yellow solid.

$^1$H-NMR (250 MHz, CHCl$_3$-d) δ 7.80 (d, J=7.1 Hz, 2H), 7.177.48 (m, 13H), 4.69 (s, 2H), 2.29 (s, 3H), 2.03 (s, 3H), 1.91 (s, 3H) ppm.

Example 6

Synthesis of 5-(benzyloxy)-3,4,6-trimethylpyridin-2-amine; 5a-2

Acetylchloride (2 mL) was added dropwise to methanol (50 mL) under ice cooling to be dissolved, and the resultant solution was added to a mixed solution of Compound 5a-1 (2 g, 4.920 mmol) including methanol (50 mL) and THF (5 mL), and the result was stirred at room temperature for 12 hours. The reaction solution was concentrated under reduced pressure, and then, diluted with EtOAc (300 mL) and washed with saturated NaHCO$_3$ solution (20 mL×4). The EtOAc solution was washed with the saturated saline water (20 mL), followed by drying with MgSO$_4$, filtering, and concentrating under reduced pressure. The residual was purified by column chromatography (CHCl$_3$:MeOH=20:1) to obtain Compound 5a-2 (992 mg, 83%) in the form of light yellow solid.

$^1$H-NMR (250 MHz, CHCl$_3$-d) δ 7.317.45 (m, 5H), 4.68 (s, 2H), 4.25 (br s, 1H), 2.34 (s, 3H), 2.16 (s, 3H), 1.99 (s, 3H) ppm.

Example 7

Synthesis of 6-amino-2,4,5-trimethylpyridin-3-ol; 6a

10% Pd/C (10 mg) was added to a methanol (2 mL) solution of Compound 5a-2 (50 mg, 0.206 mmol), and then the result was stirred under a hydrogen stream at room temperature for 3 hours. The reaction solution was filtered and the filtrate was concentrated under reduced pressure, and then the residual was dissolved in methanol (2 mL) and then the resultant solution was filtered through a syringe filter (Advantec JP050AN) and concentrated to obtain Compound 6a (31 mg, 100%) in the form of orange solid.

$^1$H-NMR (250 MHz, DMSO-d$_6$) δ 7.44 (s, 1H), 4.85 (s, 2H), 2.16 (s, 3H), 2.04 (s, 3H), 1.91 (s, 3H) ppm.

Example 8

Synthesis of 5-(benzyloxy)-N-hexyl-3,4,6-trimethyl-pyridin-2-amine; 5b

Hexylamine (0.97 mL, 7.35 mmol) was added to a toluene (25 mL) solution of Compound 4 (1.5 g, 4.90 mmol), NaO$^t$Bu (680 mg, 6.86 mmol), Pd=DBA)$_3$ (101 mg, 0.10 mmol), and BINAP (125 mg, 0.20 mmol), and then, the mixture was refluxed while stirring at a temperature of 100° C. for 2 hours. The reaction solution was cooled to room temperature and then diluted with EtOAc (500 mL) and water (10 mL), and the EtOAc solution was washed with saturated saline water (20 mL×5). The result was dried with MgSO$_4$, filtered, and concentrated under reduced pressure. The residual was purified by column chromatography (EtOAc:Hex=1:15) to obtain Compound 5b (1.58 g, 97%) in the form of yellow liquid.

$^1$H-NMR (250 MHz, CHCl$_3$-d) δ 7.34-7.48 (m, 5H), 4.69 (s, 2H), 3.47 (t, J=6.8 Hz, 2H), 2.43 (s, 3H), 2.19 (s, 3H), 1.99 (s, 3H), 1.57-1.65 (m, 2H), 1.25-1.35 (m, 6H), 0.87-0.92 (m, 3H) ppm.

Example 9

Synthesis of 6-(hexylamino)-2,4,5-trimethylpyridin-3-ol; 6b

10% Pd/C (20 mg) was added to a methanol (2 mL) solution of Compound 5b (100 mg, 0.306 mmol), and then the result was stirred under a hydrogen stream at room temperature for 5 hours. The reaction solution was filtered and the filtrate was concentrated under reduced pressure. The residual was dissolved in methanol (2 mL) and then the resultant solution was filtered through a syringe filter (Advantec JP050AN) and concentrated to obtain Compound 6b (72 mg, 99%) in the form of light yellow solid.

$^1$H-NMR (250 MHz, DMSO-d$_6$) δ 7.47 (s, 1H), 5.10 (s, 1H), 3.23 (t, J=6.8 Hz, 2H), 2.21 (s, 3H), 2.05 (s, 3H), 1.92 (s, 3H), 1.50-1.52 (m, 2H), 1.27 (m, 6H), 0.83-0.86 (m, 3H) ppm.

Example 10

Synthesis of 5-(benzyloxy)-N-hexadecyl-3,4,6-trimethylpyridin-2-amine; 5c

1-Hexadecylamine (1.96 g, 7.35 mmol) was added to a toluene (25 mL) solution of Compound 4 (1.5 g, 4.90 mmol), NaO$^t$Bu (680 mg, 6.86 mmol), Pd$_2$(DBA)$_3$ (101 mg, 0.10 mmol), and BINAP (125 mg, 0.20 mmol), and then, the mixture was refluxed while stirring at a temperature of 120° C. for 2 hours. The reaction solution was cooled to room temperature and then diluted with EtOAc (500 mL) and water (10 mL), and the EtOAc solution was washed with saturated saline water (20 mL×5). The result was dried with MgSO$_4$, filtered, and concentrated under reduced pressure. The residual was purified by column chromatography (CHCl$_3$:MeOH=9:1) to obtain Compound 5c (1.42 g, 63%) in the form of yellow solid.

$^1$H-NMR (250 MHz, CHCl$_3$-d) δ 7.24-7.49 (m, 5H), 4.69 (s, 2H), 3.44 (t, J=7.0 Hz, 2H), 2.41 (s, 3H), 2.24 (s, 3H), 2.18 (s, 3H), 1.56-1.65 (m, 2H), 1.13-1.36 (m, 26H), 0.85-0.91 (m, 3H) ppm.

Example 11

Synthesis of 6-(hexadecylamino)-2,4,5-trimethylpyridin-3-ol; 6c

10% Pd/C (20 mg) was added to a methanol (2 mL) solution of Compound 5c (100 mg, 0.214 mmol), and then the result was stirred under a hydrogen stream at room temperature for 5 hours. The reaction solution was filtered and the filtrate was concentrated under reduced pressure. The residual was dissolved in methanol (2 mL) and then the resultant solution was filtered through a syringe filter (Advantec JP050AN) and concentrated to obtain Compound 6c (73 mg, 90%) in the form of light brown solid.

$^1$H-NMR (250 MHz, CHCl$_3$-d) δ 8.98 (s, 1H), 7.29 (s, 1H), 3.36-3.45 (m 2H), 2.48 (s, 3H), 2.22 (s, 3H), 2.09 (s, 3H), 1.52-1.65 (m, 2H), 1.15-1.37 (m, 26H), 0.79-0.86 (m, 3H) ppm.

Examples 12 and 13

Synthesis of 3-((5-(benzyloxy)-3,4,6-trimethylpyridin-2-yl)amino)propan-1-ol; (5d-1)] and 5-(benzyloxy)-N-(3-((5-(benzyloxy)-3,4,6-trimethylpyridin-2-yl)oxy)propyl)-3,4,6-trimethylpyridin-2-amine; 5d-2

3-Amino-1-propanol (0.6 mL, 7.83 mmol) was added to a toluene (30 mL) solution of Compound 4 (2 g, 6.53 mmol), NaO$^t$Bu (906 mg, 9.14 mmol), Pd$_2$(DBA)$_3$ (135 mg, 0.13 mmol), and BINAP (166 mg, 0.26 mmol), and then, the mixture was refluxed while stirring at a temperature of 120° C. for 4 hours. The reaction solution was cooled to room temperature and then diluted with EtOAc (500 mL) and water (10 mL), and the EtOAc solution was washed with saturated saline water (20 mL×5). The result was dried with MgSO$_4$, filtered, and concentrated under reduced pressure. The residual was purified by column chromatography (EtOAc:Hex=1:4) to obtain Compound 5d-1 (550 mg) in the form of yellow solid and Compound 5d-2 (630 mg) in the form of light yellow solid.

5d-1: $^1$H-NMR (250 MHz, DMSO-d$_6$) δ 7.31-7.48 (m, 5H), 5.47 (t, J=5.5 Hz, 1H), 4.64 (s, 2H), 3.47 (t, J=5.5 Hz, 2H), 3.30-3.40 (m, 2H), 2.24 (s, 3H), 2.11 (s, 3H), 1.93 (s, 3H), 1.64-1.74 (m, 2H) ppm.

5d-2: $^1$H-NMR (250 MHz, DMSO-d$_6$) δ 7.30-7.47 (m, 10H), 5.49 (t, J=5.4 Hz, 1H), 4.70 (s, 2H), 4.63 (s, 2H), 4.29 (d, J=6.2 Hz, 2H), 3.44-3.51 (m, 2H), 2.29 (s, 3H), 2.24 (s, 3H), 2.14 (s, 3H), 2.10 (s, 3H), 2.06 (s, 3H), 1.94 (s, 3H) ppm.

Example 14

Synthesis of 6-((3-hydroxypropyl)amino)-2,4,5-trimethylpyridin-3-ol; 6d-1

10% Pd/C (20 mg) was added to a methanol (2 mL) solution of Compound 5d-1 (100 mg, 0.333 mmol), and then the result was stirred under a hydrogen stream at room temperature for 5 hours. The reaction solution was filtered and the filtrate was concentrated under reduced pressure. The residual was dissolved in methanol (2 mL) and then the resultant solution was filtered through a syringe filter (Advantec JP050AN) and concentrated to obtain Compound 6d-1 (70 mg, 100%) in the form of yellow liquid.

$^1$H-NMR (250 MHz, DMSO-d$_6$) δ 7.42 (s, 1H), 5.16 (s, 1H), 3.45 (t, J=6.0 Hz, 2H), 3.31 (t, J=6.4 Hz, 2H), 2.19 (s, 3H), 2.05 (s, 3H), 1.91 (s, 3H), 1.70 1.60 (m, 2H) ppm.

Example 15

Synthesis of 6-(3-((5-hydroxy-3,4,6-trimethylpyridin-2-yl)amino)propoxy)-2,4,5-trimethylpyridin-3-ol; 6d-2

10% Pd/C (20 mg) was added to a methanol (2 mL) solution of Compound 5d-2 (100 mg, 0.190 mmol), and then the result was stirred under a hydrogen stream at room temperature for 5 hours. The reaction solution was filtered and the filtrate was concentrated under reduced pressure. The residual was dissolved in methanol (2 mL) and then the resultant solution was filtered through a syringe filter (Advantec JP050AN) and concentrated to obtain Compound 6d-2 (64 mg, 97%) in the form of yellow liquid.

$^1$H-NMR (250 MHz, DMSO-d$_6$) δ 7.87 (br s, 1H), 7.43 (br s, 1H), 4.23 (t, J=6.3 Hz, 2H), 3.40 (t, J=6.3 Hz, 2H), 2.25 (s, 3H), 2.21 (s, 3H), 2.13 (s, 3H), 2.09 (s, 3H), 2.06 (s, 3H), 1.85 (s, 3H) ppm.

Example 16

Synthesis of 5-(benzyloxy)-N-cyclohexyl-3,4,6-trimethylpyridin-2-amine; 5e

Cyclohexylamine (0.81 g, 7.10 mmol) was added to a toluene (25 mL) solution of Compound 4 (1.8 g, 5.91 mmol), NaO$^t$Bu (820 mg, 8.27 mmol), Pd$_2$(DBA)$_3$ (122 mg, 0.12 mmol), and BINAP (150 mg, 0.23 mmol), and then, the mixture was refluxed while stirring at a temperature of 120° C. for 2 hours. The reaction solution was cooled to room temperature and then diluted with EtOAc (500 mL) and water (10 mL), and the EtOAc solution was washed with saturated saline water (20 mL×5). The result was dried with MgSO$_4$, filtered, and concentrated under reduced pressure. The residual was purified by column chromatography (EtOAc:Hex=1:19) to obtain Compound 5e (1.73 g, 90%) in the form of yellow solid.

$^1$H-NMR (250 MHz, CHCl$_3$-d) δ 7.29 7.48 (m, 5H), 4.68 (s, 2H), 3.92 4.01 (m, 1H), 2.38 (s, 3H), 2.16 (s, 3H), 2.04 2.11 (m, 2H), 1.95 (s, 3H), 1.09 1.77 (m, 8H) ppm.

Example 17

Synthesis of 6-(cyclohexylamino)-2,4,5-trimethylpyridin-3-ol; 6e

10% Pd/C (20 mg) was added to a methanol (2 mL) solution of Compound 5e (100 mg, 0.308 mmol), and then the result was stirred under a hydrogen stream at room temperature for 5 hours. The reaction solution was filtered and the filtrate was concentrated under reduced pressure. The residual was dissolved in methanol (2 mL) and then the resultant solution was filtered through a syringe filter (Advantec JP050AN) and concentrated to obtain Compound 6e (71 mg, 98%) in the form of yellow solid.

$^1$H-NMR (250 MHz, DMSO-d$_6$) δ 7.41 (s, 1H), 4.51 (s, 1H), 3.77 (s, 1H), 2.19 (s, 3H), 2.04 (s, 3H), 1.90 (s, 3H), 1.10 1.66 (m, 10H) ppm.

Example 18

Synthesis of N-benzyl-5-(benzyloxy)-3,4,6-trimethylpyridin-2-amine; 5f

Benzylamine (0.8 mL, 7.35 mmol) was added to a toluene (25 mL) solution of Compound 4 (1.5 g, 4.90 mmol), NaO$^t$Bu (680 mg, 6.86 mmol), Pd$_2$(DBA)$_3$ (101 mg, 0.10 mmol), and BINAP (125 mg, 0.20 mmol), and then, the mixture was refluxed while stirring at a temperature of 120° C. for 4 hours. The reaction solution was cooled to room temperature and then diluted with EtOAc (500 mL) and water (10 mL), and the EtOAc solution was washed with saturated saline water (20 mL×5). The result was dried with MgSO$_4$, filtered, and concentrated under reduced pressure. The residual was purified by column chromatography (EtOAc:Hex=1:15 AM) to obtain Compound 5f (1.6 g, 97%) in the form of yellow solid.

$^1$H-NMR (250 MHz, CHCl$_3$-d) δ 7.24 7.52 (m, 10H), 4.74 (s, 2H), 4.70 (s, 2H), 4.18 (s, 1H), 2.46 (s, 3H), 2.22 (s, 3H), 2.00 (s, 3H) ppm.

Example 19

Synthesis of 6-(benzylamino)-2,4,5-trimethylpyridin-3-ol; 6f

10% Pd/C (20 mg) was added to a methanol (2 mL) solution of Compound 5f (100 mg, 0.301 mmol), and then the result was stirred under a hydrogen stream at room temperature for 5 hours. The reaction solution was filtered and the filtrate was concentrated under reduced pressure. The residual was dissolved in methanol (2 mL) and then the resultant solution was filtered through a syringe filter (Advantec JP050AN) and concentrated to obtain Compound 6f (66 mg, 90%) in the form of yellow liquid.

$^1$H-NMR (250 MHz, DMSO-d$_6$) δ 7.15 7.34 (m, 5H), 5.69 (t, J=5.6 Hz, 1H), 4.50 (d, J=5.3 Hz, 2H), 2.17 (s, 3H), 2.06 (s, 3H), 1.97 (s, 3H) ppm.

Example 20

Synthesis of 5-(benzyloxy)-3,4,6-trimethyl-N-phenylpyridin-2-amine; 5g

Aniline (0.71 mL, 7.838 mmol) was added to a toluene (30 mL) solution of Compound 4 (2 g, 6.53 mmol), NaO$^t$Bu (906 mg, 9.14 mmol), Pd=DBA)$_3$ (135 mg, 0.13 mmol), and BINAP (166 mg, 0.26 mmol), and then, the mixture was refluxed while stirring at a temperature of 120° C. for 2 hours. The reaction solution was cooled to room temperature and then diluted with EtOAc (500 mL) and water (10 mL), and the EtOAc solution was washed with saturated saline water (20 mL×5). The result was dried with MgSO$_4$, filtered, and concentrated under reduced pressure. The residual was purified by column chromatography (EtOAc:Hex=1:20 AM) to obtain Compound 5g (1.94 g, 93%) in the form of yellow liquid.

$^1$H-NMR (250 MHz, CHCl$_3$-d) δ 7.25 7.51 (m, 9H), 6.93 6.99 (m, 1H), 6.38 (s, 1H), 4.79 (s, 2H), 2.49 (s, 3H), 2.27 (s, 3H), 2.11 (s, 3H) ppm.

Example 21

Synthesis of 2,4,5-trimethyl-6-(phenylamino)pyridin-3-ol; 6g

10% Pd/C (20 mg) was added to a methanol (2 mL) solution of Compound 5g (100 mg, 0.314 mmol), and then the result was stirred under a hydrogen stream at room temperature for 5 hours. The reaction solution was filtered and the filtrate was concentrated under reduced pressure. The residual was dissolved in methanol (2 mL) and then the resultant solution was filtered through a syringe filter (Advantec JP050AN) and concentrated to obtain Compound 6g (70 mg, 98%) in the form of light yellow solid.

$^1$H-NMR (250 MHz, DMSO-d$_6$) δ 8.07 (br s, 1H), 7.53 (s, 1H), 7.25 7.28 (m, 2H), 7.10 7.16 (m, 2H), 6.68 6.73 (m, 1H), 2.27 (s, 3H), 2.13 (s, 3H), 2.08 (s, 3H) ppm.

Example 22

Synthesis of 5-(benzyloxy)-N-(2-isopropylphenyl)-3,4,6-trimethylpyridin-2-amine; 5h 2-isopropylaniline (1.03 mL, 7.35 mmol) was added to a toluene (25 mL) solution of Compound 4 (1.5 g, 4.90 mmol), NaO$^t$Bu (680 mg, 6.86 mmol), Pd=DBA)$_3$ (101 mg, 0.10 mmol), and BINAP (125 mg, 0.20 mmol), and then, the mixture was refluxed while stirring at a temperature of 120° C. for 2 hours. The reaction solution was cooled to room temperature and then diluted with EtOAc (500 mL) and water (10 mL), and the EtOAc solution was washed with saturated saline water (20 mL×5). The result was dried with MgSO$_4$, filtered, and concentrated under reduced pressure. The residual was purified by column chromatography (CHCl$_3$:MeOH=99:1) to obtain Compound 5h (1.78 g, 99%) in the form of brown solid.

$^1$H-NMR (250 MHz, CHCl$_3$-d) δ 7.25 7.49 (m, 7H), 7.06 7.13 (m, 1H), 6.94 7.01 (m, 1H), 5.92 (s, 1H), 4.77 (s, 2H), 3.13 3.24 (m, 1H), 2.42 (s, 3H), 2.23 (s, 3H), 2.03 (s, 3H), 1.32 (s, 3H), 1.29 (s, 3H) ppm.

Example 23

Synthesis of 6-((2-isopropylphenyl)amino)-2,4,5-trimethylpyridin-3-ol; 6h

10% Pd/C (20 mg) was added to a methanol (2 mL) solution of Compound 5h (100 mg, 0.277 mmol), and then the result was stirred under a hydrogen stream at room temperature for 5 hours. The reaction solution was filtered and the filtrate was concentrated under reduced pressure. The residual was dissolved in methanol (2 mL) and then the resultant solution was filtered through a syringe filter (Advantec JP050AN) and concentrated to obtain Compound 6h (72 mg, 96%) in the form of yellow solid.

$^1$H-NMR (250 MHz, DMSO-d$_6$) δ 7.19 (d, J=7.4 Hz, 1H), 6.77 7.01 (m, 4H), 3.11 3.22 (m, 1H), 2.20 (s, 3H), 2.13 (s, 3H), 2.02 (s, 3H), 1.17 (s, 3H), 1.14 (s, 3H) ppm.

Example 24

Synthesis of 5-(benzyloxy)-3,4,6-trimethyl-N-(4-nitrophenyl)pyridin-2-amine; 5i 4-nitroaniline (1.03 mL, 7.35 mmol) was added to a toluene (25 mL) solution of Compound 4 (2.18 g, 7.12 mmol), NaO$^t$Bu (987 mg, 9.96 mmol), Pd=DBA)$_3$ (147 mg, 0.14 mmol), and BINAP (177 mg, 0.28 mmol), and then, the mixture was refluxed while stirring at a temperature of 120° C. for 6 hours. The reaction solution was cooled to room temperature and then diluted with EtOAc (500 mL) and water (10 mL), and the EtOAc solution was washed with saturated saline water (20 mL×5). The result was dried with MgSO$_4$, filtered, and concentrated under reduced pressure. The residual was purified by column chromatography (CHCl$_3$ only) to obtain Compound 5i (2.36 g, 91%) in the form of yellow solid.

$^1$H-NMR (250 MHz, CHCl$_3$-d) δ 8.12 (dd, J=7.2, 1.9 Hz, 2H), 7.35 7.46 (m, 7H), 6.50 (s, 1H), 4.77 (s, 2H), 2.46 (s, 3H), 2.24 (s, 3H), 2.15 (s, 3H) ppm.

Example 25

Synthesis of 2,4,5-trimethyl-6-((4-nitrophenyl)amino)pyridin-3-ol; 6i

A 1 M BCl$_3$ (0.55 mL, 0.55 mmol) solution was added dropwise to a CH$_2$Cl$_2$ (3 mL) solution of Compound 5i (100 mg, 0.275 mmol) and pentamethylbenzene (122.4 mg, 0.825 mmol) under ice cooling, and then the mixture was stirred for 30 minutes. A CHCl$_3$:MeOH=9:1 solution (1 mL) was added to the reaction solution and then, the result was stirred at room temperature for 1 hour. The resultant reaction solution was concentrated under reduced pressure, and the residual was purified by column chromatography (CHCl$_3$:MeOH=9:1) to obtain Compound 6i (56 mg, 74%) in the form of yellow solid.

$^1$H-NMR (250 MHz, DMSO-d$_6$) δ 8.86 (s, 1H), 8.44 (s, 1H), 8.03 (d, J=9.1 Hz, 2H), 7.21 (d, J=9.1 Hz, 2H), 2.31 (s, 3H), 2.15 (s, 3H), 2.10 (s, 3H) ppm.

Example 26

Synthesis of 5-(benzyloxy)-N-(4-bromophenyl)-3,4,6-trimethylpyridin-2-amine; 5j

4-Bromoamine (869 mg, 4.90 mmol) was added to a toluene (25 mL) solution of Compound 4 (1.5 g, 4.90 mmol), NaO$^t$Bu (680 mg, 6.86 mmol), Pd$_2$(DBA)$_3$ (101 mg, 0.10 mmol), and BINAP (125 mg, 0.20 mmol), and then, the mixture was refluxed while stirring at a temperature of 120° C. for 6 hours. The reaction solution was cooled to room temperature and then diluted with EtOAc (500 mL) and water (10 mL), and the EtOAc solution was washed with saturated saline water (20 mL×5). The result was dried with MgSO$_4$, filtered, and concentrated under reduced pressure. The residual was purified by column chromatography (EtOAc:Hex=1:9) to obtain target compound 5j (1.23 g, 63%) in the form of yellow solid.

$^1$H-NMR (250 MHz, CHCl$_3$-d) δ 7.25 7.48 (m, 9H), 6.02 (s, 1H), 4.74 (s, 2H), 2.42 (s, 3H), 2.22 (s, 3H), 2.09 (s, 3H) ppm.

Example 27

Synthesis of 6-((4-bromophenyl)amino)-2,4,5-trimethylpyridin-3-ol; 6j

A 1 M BCl$_3$ (0.5 mL, 0.503 mmol) solution was added dropwise to a CH$_2$Cl$_2$ (3 mL) solution of Compound 5j (100 mg, 0.251 mmol) and pentamethylbenzene (112 mg, 0.755 mmol) under ice cooling, and then the mixture was stirred for 30 minutes. A CHCl$_3$:MeOH=9:1 solution (1 mL) was added to the reaction solution and then, the result was stirred at room temperature for 1 hour. The resultant reaction solution was concentrated under reduced pressure, and the residual was purified by column chromatography (CHCl$_3$:MeOH=9:1) to obtain Compound 6j (75 mg, 97%) in the form of yellow solid.

¹H-NMR (250 MHz, DMSO-d₆) δ 8.44 (br s, 1H), 7.99 (s, 1H), 7.30 (d, J=8.9 Hz, 2H), 7.19 (d, J=8.9 Hz, 2H), 2.30 (s, 3H), 2.16 (s, 3H), 2.09 (s, 3H) ppm.

Example 28

Synthesis of
2,4,5-trimethyl-6-(phenylamino)pyridin-3-ol
hydrobromide; (6g-HBr)

10% Pd/C (20 mg) was added to a MeOH and THF (1:1) (2 mL) solution of Compound 5j (100 mg, 0.251 mmol), and under a hydrogen stream, the mixture was stirred at room temperature for 5 hours. The reaction solution was filtered and the filtrate was concentrated under reduced pressure. The residual was dissolved in methanol (2 mL) and then the resultant solution was filtered through a syringe filter (Advantec JP050AN) and concentrated to obtain Compound 6g-HBr (76 mg, 98%) in the form of yellow solid.
¹H-NMR (250 MHz, DMSO-d₆) δ 9.63 (br s, 1H), 8.82 (br s, 1H), 7.25–7.31 (m, 2H), 6.92–7.02 (m, 3H), 2.44 (s, 3H), 2.32 (s, 3H), 2.17 (s, 3H) ppm.

Example 29

Synthesis of N-(benzo[d][1,3]dioxol-5-yl)-5-(benzyloxy)-3,4,6-trimethylpyridin-2-amine; 5k 3,4-(Methylenedioxy)aniline (1.01 g, 7.35 mmol) was added to a toluene (25 mL) solution of Compound 4 (1.5 g, 4.90 mmol), NaOᵗBu (680 mg, 6.86 mmol), Pd₂(DBA)₃ (101 mg, 0.10 mmol), and BINAP (125 mg, 0.20 mmol), and then, the mixture was refluxed while stirring at a temperature of 120° C. for 2 hours. The reaction solution was cooled to room temperature and then diluted with EtOAc (500 mL) and water (10 mL), and the EtOAc solution was washed with saturated saline water (20 mL×5). The result was dried with MgSO₄, filtered, and concentrated under reduced pressure. The residual was purified by column chromatography (EtOAc:Hex=1:9) to obtain Compound 5k (1.57 g, 88%) in the form of brown solid.
¹H-NMR (250 MHz, CHCl₃-d) δ 7.33–7.47 (m, 5H), 7.17 (d, J=2.0 Hz, 1H), 6.61–6.72 (m, 2H), 5.89 (s, 3H), 4.73 (s, 2H), 2.41 (s, 3H), 2.20 (s, 3H), 2.07 (s, 3H) ppm.

Example 30

Synthesis of 6-(benzo[d][1,3]dioxol-5-ylamino)-2,4,5-trimethylpyridin-3-ol; 6k

10% Pd/C (20 mg) was added to a methanol (2 mL) solution of Compound 5k (100 mg, 0.276 mmol), and then the result was stirred under a hydrogen stream at room temperature for 5 hours. The reaction solution was filtered and the filtrate was concentrated under reduced pressure. The residual was dissolved in methanol (2 mL) and then the resultant solution was filtered through a syringe filter (Advantec JP050AN) and concentrated to obtain Compound 6k (75 mg, 100%) in the form of brown solid.
¹H-NMR (250 MHz, DMSO-d₆) δ 7.33 (s, 1H), 7.11 (s, 1H), 6.71 (s, 2H), 5.87 (s, 2H), 2.24 (s, 3H), 2.10 (s, 3H), 2.05 (s, 3H) ppm.

Example 31

Synthesis of 5-(benzyloxy)-3,4,6-trimethyl-N,N-diphenylpyridin-2-amine; 5l

Diphenylamine (829 mg, 4.90 mmol) was added to a toluene (25 mL) solution of Compound 4 (1.5 g, 4.90 mmol), NaOᵗBu (680 mg, 6.86 mmol), Pd₂(DBA)₃ (101 mg, 0.10 mmol), and BINAP (125 mg, 0.20 mmol), and then, the mixture was refluxed while stirring at a temperature of 120° C. for 6 hours. The reaction solution was cooled to room temperature and then diluted with EtOAc (500 mL) and water (10 mL), and the EtOAc solution was washed with saturated saline water (20 mL×5). The result was dried with MgSO₄, filtered, and concentrated under reduced pressure. The residual was purified by column chromatography (EtOAc:Hex=1:9) to obtain Compound 5l (695 mg, 36%) in the form of brown liquid.
¹H-NMR (250 MHz, CHCl₃-d) δ 7.35–7.49 (m, 5H), 7.17–7.23 (m, 5H), 6.89–6.96 (m, 5H), 4.83 (s, 2H), 2.42 (s, 3H), 2.21 (s, 3H), 1.94 (s, 3H) ppm.

Example 32

Synthesis of
6-(diphenylamino)-2,4,5-trimethylpyridin-3-ol; 6l

10% Pd/C (20 mg) was added to a MeOH and THF (1:1) (2 mL) solution of Compound 5l (100 mg, 0.253 mmol), and under a hydrogen stream, the mixture was stirred at room temperature for 5 hours. The reaction solution was filtered and the filtrate was concentrated under reduced pressure. The residual was dissolved in methanol (2 mL) and then the resultant solution was filtered through a syringe filter (Advantec JP050AN) and concentrated to obtain Compound 6l (68 mg, 87%) in the form of yellow solid.
¹H-NMR (250 MHz, DMSO-d₆) δ 7.16–7.22 (m, 4H), 6.79–6.98 (m, 6H), 2.28 (s, 3H), 2.13 (s, 3H), 1.91 (s, 3H) ppm.

Example 33

Synthesis of 3-(benzyloxy)-2,4,5-trimethyl-6-(pyrrolidin-1-yl)pyridine; 5m

Pyrrolidine (0.40 mL, 4.90 mmol) was added to a toluene (25 mL) solution of Compound 4 (1.5 g, 4.90 mmol), NaOᵗBu (680 mg, 6.86 mmol), Pd₂(DBA)₃ (101 mg, 0.10 mmol), and BINAP (125 mg, 0.20 mmol), and then, the mixture was refluxed while stirring at a temperature of 120° C. for 4 hours. The reaction solution was cooled to room temperature and then diluted with EtOAc (500 mL) and water (10 mL), and the EtOAc solution was washed with saturated saline water (20 mL×5). The result was dried with MgSO₄, filtered, and concentrated under reduced pressure. The residual was purified by column chromatography (EtOAc:Hex=1:9) to obtain Compound 5m (1.04 g, 71%) in the form of yellow liquid.
¹H-NMR (250 MHz, CHCl₃-d) δ 7.33–7.48 (m, 5H), 4.71 (s, 2H), 3.36 (t, J=6.7 Hz, 4H), 2.41 (s, 3H), 2.18 (s, 3H), 2.14 (s, 3H), 1.85–1.93 (m, 4H) ppm.

Example 34

Synthesis of
2,4,5-trimethyl-6-(pyrrolidin-1-yl)pyridin-3-ol; 6m

10% Pd/C (20 mg) was added to a methanol (2 mL) solution of Compound 5m (100 mg, 0.337 mmol), and then the result was stirred under a hydrogen stream at room temperature for 10 hours. The reaction solution was filtered and the filtrate was concentrated under reduced pressure. The residual was dissolved in methanol (2 mL) and then the resultant solution was filtered through a syringe filter (Advantec JP050AN) and concentrated to obtain Compound 6m (70 mg, 100%) in the form of pink liquid.

$^1$H-NMR (250 MHz, DMSO-$d_6$) δ 8.04 (br s, 1H), 3.23 (t, J=6.5 Hz, 4H), 2.27 (s, 3H), 2.10 (s, 6H), 1.78˜1.84 (m, 4H) ppm.

Example 35

Synthesis of 1-(5-(benzyloxy)-3,4,6-trimethylpyridin-2-yl)-4-methylpiperazine; 5n N-methylpiperazine (0.73 mL, 6.53 mmol) was added to a toluene (30 mL) solution of Compound 4 (2 g, 6.53 mmol), NaO$^t$Bu (906 mg, 9.14 mmol), Pd$_2$(DBA)$_3$ (135 mg, 0.13 mmol), and BINAP (166 mg, 0.26 mmol), and then, the mixture was refluxed while stirring at a temperature of 120° C. for 6 hours. The reaction solution was cooled to room temperature and then diluted with EtOAc (500 mL) and water (10 mL), and the EtOAc solution was washed with saturated saline water (20 mL×5). The result was dried with MgSO$_4$, filtered, and concentrated under reduced pressure. The residual was purified by column chromatography (CHCl$_3$:MeOH=20:1) to obtain Compound 5n (918 mg, 43%) in the form of yellow solid.

$^1$H-NMR (250 MHz, CHCl$_3$-d) δ 7.32˜7.47 (m, 5H), 4.71 (s, 2H), 3.07 (t, J=4.7 Hz, 4H), 2.55 (br s, 4H), 2.41 (s, 3H), 2.33 (s, 3H), 2.16 (s, 3H), 2.14 (s, 3H) ppm.

Example 36

Synthesis of 2,4,5-trimethyl-6-(4-methylpiperazin-1-yl)pyridin-3-ol; 6n

10% Pd/C (20 mg) was added to a methanol (2 mL) solution of Compound 5n (100 mg, 0.307 mmol), and then the result was stirred under a hydrogen stream at room temperature for 2 hours. The reaction solution was filtered and the filtrate was concentrated under reduced pressure. The residual was dissolved in methanol (2 mL) and then the resultant solution was filtered through a syringe filter (Advantec JP050AN) and concentrated to obtain Compound 6n (72 mg, 99%) in the form of yellow solid.

$^1$H-NMR (250 MHz, DMSO-$d_6$) δ 2.87 (t, J=4.7 Hz, 4H), 2.50 (t, J=1.9 Hz, 4H), 2.27 (s, 3H), 2.25 (s, 3H), 2.08 (s, 6H) ppm.

Example 37

Synthesis of 4-(5-(benzyloxy)-3,4,6-trimethylpyridin-2-yl)morpholine; 5o

Morpholine (0.59 mL, 6.53 mmol) was added to a toluene (30 mL) solution of Compound 4 (2 g, 6.53 mmol), NaO$^t$Bu (906 mg, 9.14 mmol), Pd$_2$(DBA)$_3$ (135 mg, 0.13 mmol), and BINAP (166 mg, 0.26 mmol), and then, the mixture was refluxed while stirring at a temperature of 120° C. for 5 hours. The reaction solution was cooled to room temperature and then diluted with EtOAc (500 mL) and water (10 mL), and the EtOAc solution was washed with saturated saline water (20 mL×5). The result was dried with MgSO$_4$, filtered, and concentrated under reduced pressure. The residual was purified by column chromatography (EtOAc:Hex=1:9) to obtain target compound 5o (1.38 g, 67%) in the form of yellow solid.

$^1$H-NMR (250 MHz, CHCl$_3$-d) δ 7.33˜7.47 (m, 5H), 4.72 (s, 2H), 3.83 (t, J=4.6 Hz, 4H), 3.03 (t, J=4.6 Hz, 4H), 2.42 (s, 3H), 2.17 (s, 3H), 2.16 (s, 3H) ppm.

Example 38

Synthesis of 2,4,5-trimethyl-6-morpholinopyridin-3-ol; 6o

10% Pd/C (20 mg) was added to a methanol (2 mL) solution of Compound 5o (100 mg, 0.320 mmol), and then the result was stirred under a hydrogen stream at room temperature for 2 hours. The reaction solution was filtered and the filtrate was concentrated under reduced pressure. The residual was dissolved in methanol (2 mL) and then the resultant solution was filtered through a syringe filter (Advantec JP050AN) and concentrated to obtain Compound 6o (71 mg, 99%) in the form of yellow solid.

$^1$H-NMR (250 MHz, DMSO-$d_6$) δ 3.69 (t, J=4.5 Hz, 4H), 2.83 (t, J=4.6 Hz, 4H), 2.27 (s, 3H), 2.10 (s, 3H), 2.08 (s, 3H) ppm.

Example 39

Synthesis of 3-(benzyloxy)-2,4,5-trimethyl-6-(1H-pyrrol-1-yl)pyridine; 5p

Pyrrole (0.45 mL, 6.53 mmol) was added to a toluene (30 mL) solution of Compound 4 (2 g, 6.53 mmol), NaO$^t$Bu (906 mg, 9.14 mmol), Pd$_2$(DBA)$_3$ (135 mg, 0.13 mmol), and BINAP (166 mg, 0.26 mmol), and then, the mixture was refluxed while stirring at a temperature of 120° C. for 12 hours. The reaction solution was cooled to room temperature and then diluted with EtOAc (500 mL) and water (10 mL), and the EtOAc solution was washed with saturated saline water (20 mL×5). The result was dried with MgSO$_4$, filtered, and concentrated under reduced pressure. The residual was purified by column chromatography (EtOAc:Hex=1:9) to obtain target compound 5p (1.43 g, 75%) n the form of light yellow solid.

$^1$H-NMR (250 MHz, CHCl$_3$-d) δ 7.36˜7.50 (m, 5H), 6.96 (t, J=2.1 Hz, 2H), 6.30 (t, J=2.1 Hz, 2H), 4.82 (s, 2H), 2.49 (s, 3H), 2.27 (s, 3H), 2.14 (s, 3H) ppm.

Example 40

Synthesis of 2,4,5-trimethyl-6-(1H-pyrrol-1-yl)pyridin-3-ol; 6p

10% Pd/C (20 mg) was added to a methanol (2 mL) solution of Compound 5p (100 mg, 0.342 mmol), and then the result was stirred under a hydrogen stream at room temperature overnight. The reaction solution was filtered and the filtrate was concentrated under reduced pressure. The residual was dissolved in methanol (2 mL) and then the resultant solution was filtered through a syringe filter (Advantec JP050AN) and concentrated to obtain Compound 6p (69 mg, 100%) in the form of yellow solid.

$^1$H-NMR (250 MHz, DMSO-$d_6$) δ 8.79 (s, 1H), 6.90 (t, J=2.0 Hz, 2H), 6.15 (t, J=2.0 Hz, 2H), 2.34 (s, 3H), 2.18 (s, 3H), 2.00 (s, 3H) ppm.

Example 41

Synthesis of 5-(benzyloxy)-N,3,4,6-tetramethyl-N-(pyridin-2-yl)pyridin-2-amine; 5q 2-(Methylamino)pyridine (0.68 mL, 6.53 mmol) was added to a toluene (30 mL) solution of Compound 4 (2 g, 6.53 mmol), NaO$^t$Bu (906 mg, 9.14 mmol), Pd$_2$(DBA)$_3$ (135 mg, 0.13 mmol), and BINAP (166 mg, 0.26 mmol), and then, the mixture was refluxed while stirring at a temperature of 120° C. for 12 hours. The reaction solution was cooled to room temperature and then diluted with EtOAc (500 mL) and water (10 mL), and the EtOAc solution was washed with saturated saline water (20 mL×5). The result was dried with MgSO$_4$, filtered, and concentrated under reduced pressure. The residual was purified by column chromatography (CHCl$_3$:MeOH=50:1) to obtain Compound 5q (1.78 g, 81%) in the form of yellow liquid.

$^1$H-NMR (250 MHz, CHCl$_3$-d) δ 8.178.20 (m, 1H), 7.307.48 (m, 6H), 6.556.58 (m, 1H), 6.11 (d, J=8.5 Hz, 1H), 4.82 (s, 2H), 3.40 (s, 3H), 2.47 (s, 3H), 2.23 (s, 3H), 1.98 (s, 3H) ppm.

Example 42

Synthesis of 2,4,5-trimethyl-6-(methyl(pyridin-2-yl) amino)pyridin-3-ol; 6q

10% Pd/C (20 mg) was added to a methanol (2 mL) solution of Compound 5q (100 mg, 0.299 mmol), and then the result was stirred under a hydrogen stream at room temperature for 10 hours. The reaction solution was filtered, and the filtrate was concentrated under reduced pressure. The residual was dissolved in methanol (2 mL) and then the resultant solution was filtered through a syringe filter (Advantec JP050AN) and concentrated to obtain Compound 6q (72 mg, 98%) in the form of yellow solid.

$^1$H-NMR (250 MHz, DMSO-d$_6$) δ 9.48 (br s, 1H), 8.07 (d, J=4.2 Hz, 1H), 7.567.66 (m, 1H), 6.80 (t, J=6.0 Hz, 1H), 6.40 (d, J=8.6 Hz, 2H), 3.33 (s, 3H), 2.40 (s, 3H), 2.23 (s, 3H), 1.98 (s, 3H) ppm.

Experimental Example 1

Examination of Angiogenesis Inhibiting Effects Through Chorioallantoic Membrane (CAM) Assay To examine angiogenesis inhibiting effects in vivo, CAM assay was performed (Nguyen Metal., *Microvascular Res.*, 47, pp 31-40, 1994).

Hen's fertile eggs were incubated at a temperature of 37° C. and in relative humidity 55%, and on the 10th day after the incubation, an air sac site was punched by using a hypodermic needle (Greencross Medical Science Corp, Korea) to form a first hole, and then, a planar site of the fertile egg where a window was to be formed was punched to form a second hole.

Air was removed through the first pore of the air sac site to allow the chorioallantoic membrane (CAM) to be separated from the shell of the fertile egg, and this site was cut by using a grinding wheel (Multipro 395JA, Dremel, Mexico) to form a window.

Then, a whatman filter disc (#1, whatman Co., U.S.A.) was treated with 3 mg/ml of cortisone acetate and then dried, and then, wetted with vascular endothelial growth factor (VEGF) having a concentration of 20 ng/CAM.

Through the window, the filter disc was placed on blood vessels, which were then treated with the compounds each dissolved in dimethylsulfoxide (DMSO) and diluted with phosphate buffer solution (PBS) at various concentrations.

3 days after the treatment with the compounds, the CAM site with the filter disc placed thereon was separated, and then washed with a phosphate buffer solution, and an image thereof was obtained by using a stereomicroscope (Stemi SV6 stereomicroscope, Carl Zeiss, Germany) and image-Pro Plus software (Media Cybernetics; Silver Spring, Md., U.S.A.) to count the number of blood vessel branches, and the obtained results were assayed.

As a result, as shown in Table 1 below, it was confirmed that the increase in VEGF-derived neoangiogenesis was concentration-dependently decreased due to the treatment with the compounds according to the present invention. In particular, angiogenesis inhibiting effects of Compound 6a were compared with SU4312, batimastat and α-tocopherol, and the comparison results show that Compound 6a showed excellent angiogenesis inhibiting effects even at low concentration compared to the other compounds. Compounds 6d-2, 6g, 6k, 6l, and 6m also showed excellent angiogenesis inhibiting effects.

TABLE 1

| | Test group | Number of blood vessel branches/ main blood vessel | Inhibition ratio |
|---|---|---|---|
| | PBS | 14.4 ± 2.7 | |
| | VEGF (20 ng/CAM) | 52.2 ± 2.7 | |
| VEGF (50 ng/ CAM) + | SU4312 (1.0 µg/CAM, 378 µM) | 24 ± 4.6[8] | 74.6 ± 12.1[8] |
| | Batimastat (1.0 µg/CAM, 200 µM) | 19.9 ± 2.87[8] | 78.4 ± 7.4[8] |
| | α-Tocopherol (3.0 ng/CAM, 0.7 µM) | 32.3 ± 3.5 | 45.1 ± 9.3[8] |
| | α-Tocopherol (100 ng/CAM, 23 µM) | 24.3 ± 2.7[8] | 64.4 ± 14.2[8] |
| | 6a (0.15 ng/CAM, 0.1 µM) | 28 ± 3.3[8] | 64.0 ± 8.8[8] |
| | 6a (1.5 ng/CAM, 1 µM) | 23.3 ± 2.0[8] | 76.3 ± 5.2[8] |
| | 6b (3.0 ng/CAM, 1.3 µM) | 26.3 ± 2.0[8] | 53.7 ± 10.3[8] |
| | 6c (3.0 ng/CAM, 0.8 µM) | 30.8 ± 3.8[8] | 30.1 ± 20.0[8] |
| | 6d-1 (3.0 ng/CAM, 1.4 µM) | 27.8 ± 2.3[8] | 46.3 ± 12.0[8] |
| | 6d-2 (3.5 ng/CAM, 1.0 µM) | 26.2 ± 4.4[8] | 67.3 ± 13.9[8] |
| | 6e (3.0 ng/CAM, 1.3 µM) | 35.3 ± 4.0[8] | 36.8 ± 10.7[8] |
| | 6f (3.0 ng/CAM, 1.2 µM) | 25.8 ± 3.2[8] | 56.7 ± 16.8[8] |
| | 6g (3.0 ng/CAM, 1.3 µM) | 23.3 ± 1.1[8] | 69.4 ± 5.7[8] |
| | 6g-HBr (3.0 ng/CAM, 1.0 µM) | 28.6 ± 3.9[8] | 55.0 ± 10.6[8] |
| | 6h (3.0 ng/CAM, 1.1 µM) | 28.4 ± 2.7[8] | 55.3 ± 20.3[8] |
| | 6i (3.0 ng/CAM, 1.0 µM) | 26.3 ± 1.6[8] | 74.9 ± 4.9[8] |
| | 6j (3.0 ng/CAM, 1.0 µM) | 30.7 ± 2.6[8] | 61.7 ± 7.7[8] |
| | 6k (3.0 ng/CAM, 1.1 µM) | 25.8 ± 4.3[8] | 62.4 ± 11.6 |
| | 6l (3.0 ng/CAM, 1.0 µM) | 26.8 ± 4.6[8] | 65.4 ± 14.6 |
| | 6m (2.0 ng/CAM, 1.0 µM) | 27.6 ± 4.2[8] | 60.5 ± 12.7 |
| | 6n (2.0 ng/CAM, 1.0 µM) | 39.8 ± 6.8[8] | 24.7 ± 21.3[8] |
| | 6o (2.0 ng/CAM, 1.0 µM) | 28.8 ± 3.7[8] | 59.0 ± 11.0[8] |
| | 6p (2.0 ng/CAM, 1.0 µM) | 33.6 ± 5.5[8] | 44.0 ± 17.2[8] |
| | 6q (2.4 ng/CAM, 1.0 µM) | 34.2 ± 6.9[8] | 42.2 ± 21.7[8] |

Figure 3:
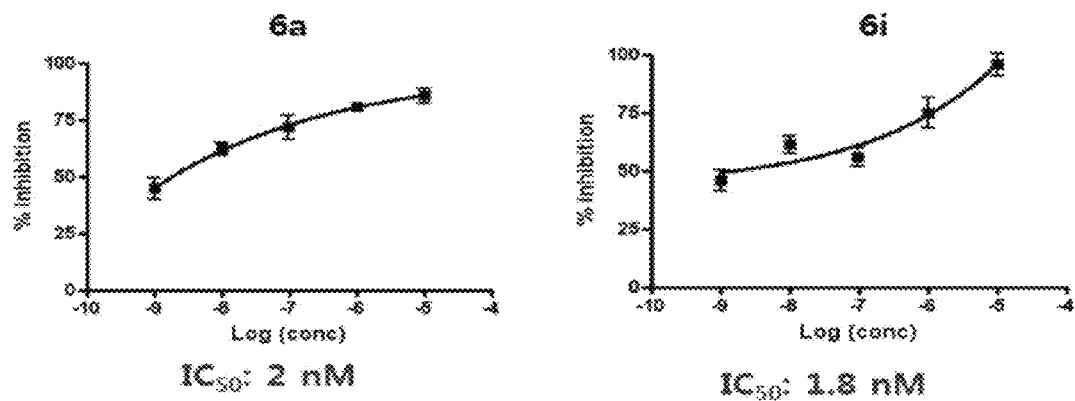
FIG. 3 shows IC50 with respect to angiogenesis inhibition of Compounds 6a and 6i.

CAM was treated with various concentrations of Compounds 6a and 6i, and IC50 thereof was measured. The results were 2 nM and 1.8 nM as shown in FIG. 3.

Experimental Example 2

Oncogenesis-Derived Angiogenesis and Tumor Growth Inhibition Effects

Hen's fertile eggs were incubated, and on the 9$^{th}$ day, a window was formed in the same manner as in Experimental Example 1, and instead of a disc, A549 lung cancer cells were mixed with matrigel at a ratio of 1:1, and then the cells were treated with Compounds 6a and 6i and inoculated at a concentration of 1.5×10$^6$ cell/CAM. Five days after the inoculation, the CAM site where tumors developed was separated and washed with a phosphate buffer solution, and then, an image thereof was obtained by using a stereomicroscope (Stemi SV6 stereomicroscope, Carl Zeiss, Germany) and Image-Pro Plus software (Media Cybernetics; Silver Spring, Md., U.S.A.) to count the number of blood vessel branches, and the results were assayed.

Figure 4:
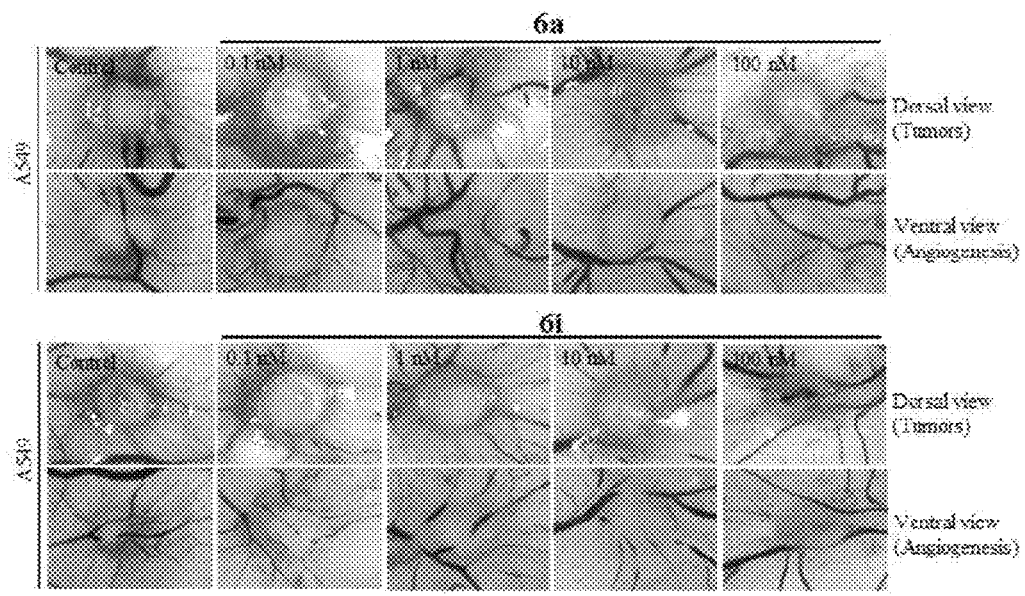
FIG. 4 shows angiogenesis caused by oncogenesis and tumor growth inhibition effects of Compounds 6a and 6i after CAM was inoculated with A549 lung cancer cells.

As a result, it was confirmed that as shown in FIG. 4, due to the treatment with various concentrations of Compounds 6a and 6i, oncogenesis-derived angiogenesis was inhibited and tumor growth was also inhibited.

Experimental Example 3

Measuring of VEGF-Derived Reactive Oxygen Species (ROS) Scavenging Ability in HUVEC Cells DCF-DA (2',7'-dichlorofluorescein diacetate) was used to measure a VEGF-derived ROS scavenging ability in HUVEC cells. When ROS exists in cells, DCF-DA is oxidized into fluorescent DCF, thereby emitting green fluorescent light. 1×10$^5$ concentration of HUVEC was spread onto a 0.2% gelatin coated 8-well plate, and then incubated for 24 hours. The cells were pretreated with Compounds 6a or 6i for 3 hours and then, treated with VEGF for 15 minutes, and then, washed three times with PBS (pH 7.4), and then, 10 µM of DCF-DA was added to EBM-2 medium, which was then placed in dark condition for 30 minutes. Then, the cells were washed three times with PBS, and a degree of intracellular fluorescence was measured by using a fluorescent microscope.

Figure 5:
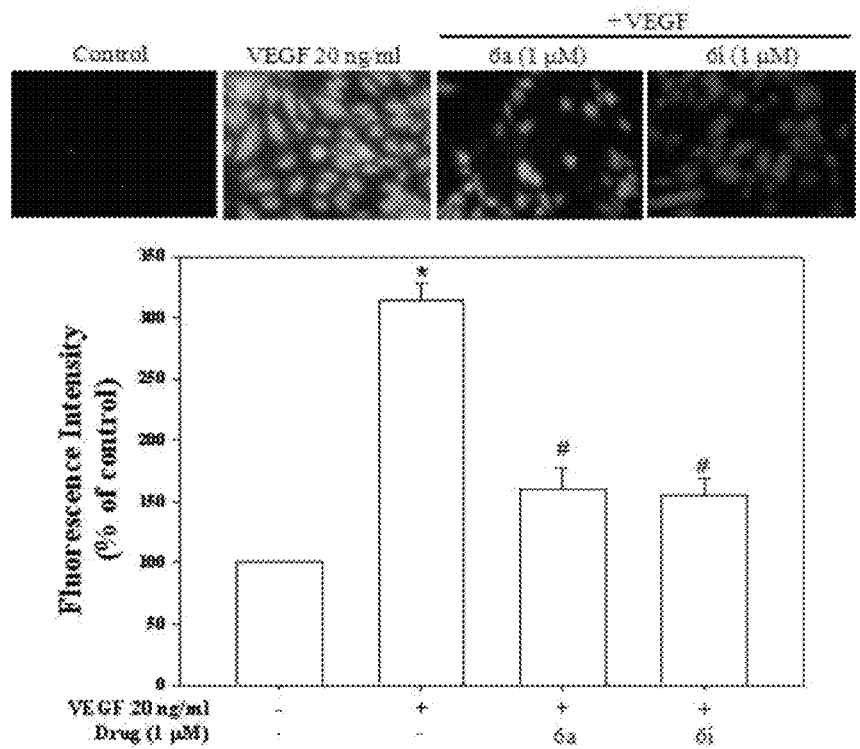
FIG. 5 shows results of VEGF-derived ROS scavenging ability of Compounds 6a and 6i.

As a result, as shown in FIG. 5, when treated with Compounds 6a or 6i, compared to VEGF, the cells showed a substantial decrease in the degree of intracellular fluorescence.

Experimental Example 4

Measuring of Macular Degeneration Risk Factor-Derived ROS Scavenging Ability

The same experiment as used in Experimental Example 3 was performed, except that ARPE-19 (adult retinal pigment epithelium-19) cell line was treated with 4-hydroxynonenal (4-HNE) or angiotensin II (Ang II), which are macular degeneration risk factors, to identify ROS scavenging ability of Compound 6a.

Figure 6:
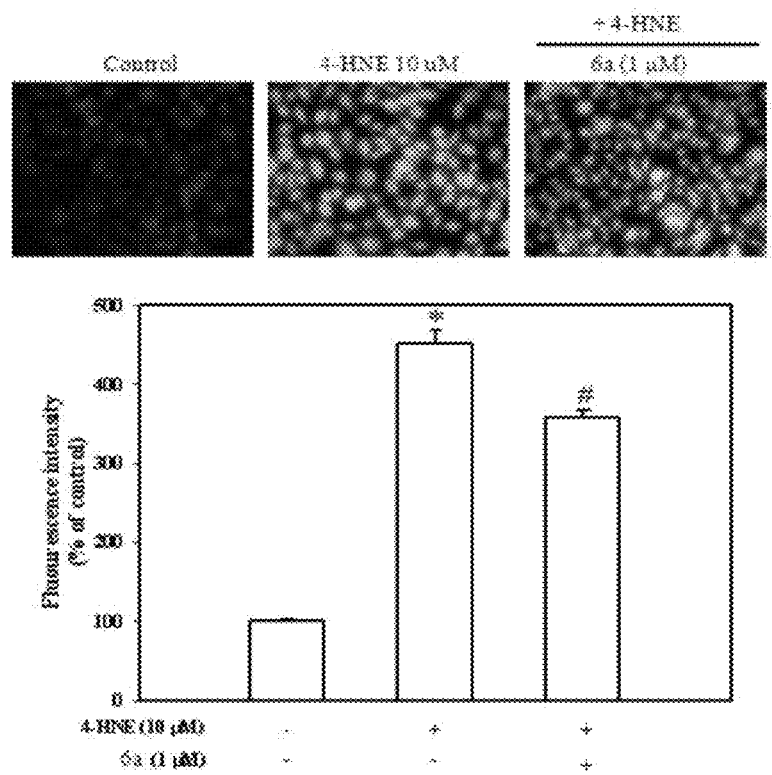
FIG. 6 shows results of ROS scavenging ability of Compound 6a obtained by treating ARPE-19 cell line with angiotensin II (Ang II) that is a macular degeneration risk factor.
Figure 7:
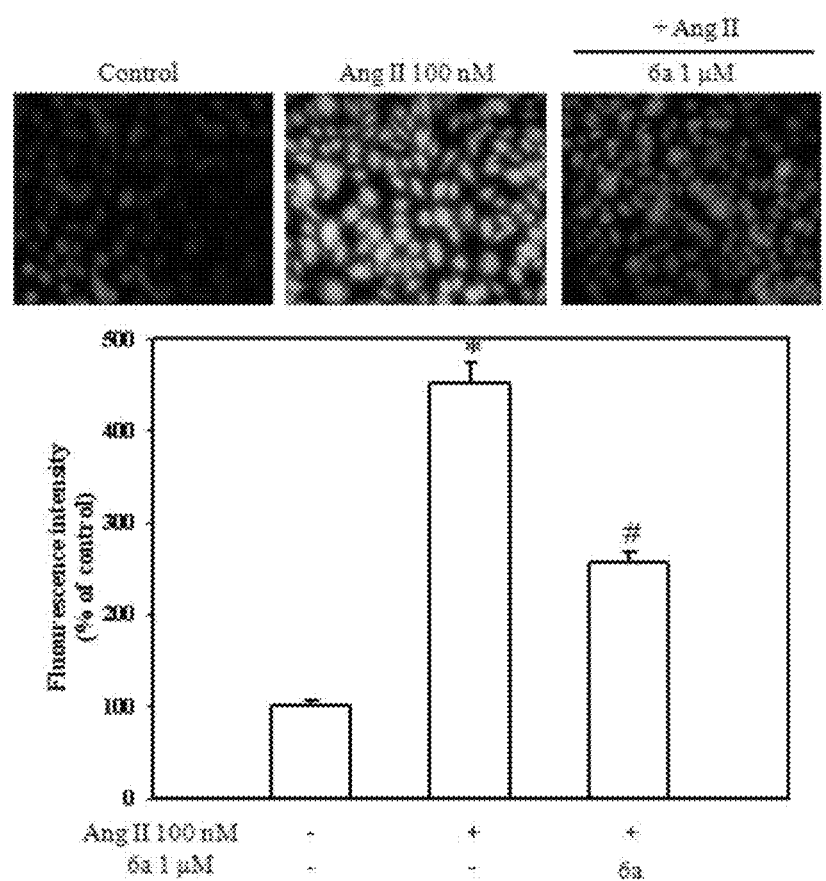
FIG. 7 shows results of ROS scavenging ability of Compound 6a obtained by treating ARPE-19 cell line with 4-hydroxynonenal (4-HNE) that is a macular degeneration risk factor.

As a result, as shown in FIGS. 6 and 7, when treated with Compound 6a, compared to a control, a degree of intracellular fluorescence was substantially decreased. 4-HNE or Ang II, which are macular degeneration risk factors, causes cell injury due to the generation of ROS in ARPE cells, ultimately, Bruch's membrane damage and angiogenesis to induce macular degeneration and blindness. These experimental results show that Compound 6a strongly inhibited ROS generation of 4-HNE and Ang II to effectively treat macular degeneration.

Experimental Example 5

Toxicity Test

Male Balb/c mice were orally administered once with Compound 6a suspended in a 0.5% methylcellose solution, in a dosage of each of 0.5 g/kg, 1 g/kg, and 2 g/kg, and then, for 7 days, the survival rate and body weight of the mice were measured.

After the administration, the death, clinical symptoms, and body weight change of the mice were analyzed, and a hematological examination and a blood biochemical examination were performed. Then, the autopsy of the mice was performed, and abnormality of abdominal cavity organs and thoracic cavity organs was examined.

Examination results show that all the animals did not have distinguishing clinical symptoms or did not die, and even body weight change, blood examination, blood biochemical examination, and autopsy results showed no toxicity change.

As described above, the compounds according to the present invention did not show any toxicity change in mice up to the dosage of 2 g/kg, and accordingly, since the compounds have an oral administration lethal dose (LD50) of 2 g/kg or more, the compounds are considered as a safe material.

Hereinafter, Preparation Examples for the preparation of a composition including Compound 6a will be described. However, the Preparation Examples do not limit the present invention and are presented herein for illustrative purpose only.

Preparation Example 1

Preparation of Powder Formulation 20 mg of Compound 6a, 100 mg of lactose, and 10 mg of talc were mixed, and a sealed bag was filled with the mixture to prepare a powder formulation.

Preparation Example 2

Preparation of Tablet Formulation 20 mg of Compound 6a, 100 mg of corn starch, 100 mg of lactose, and 2 mg of magnesium stearate were mixed, and then, the mixture was compressed according to a conventional tablet preparation method to form a tablet formulation.

Preparation Example 3

Preparation of Capsule Formulation 10 mg of Compound 6a, 100 mg of corn starch, 100 mg of lactose, and 2 mg of magnesium stearate were mixed, and then, the components were mixed according to a conventional capsule preparation method. A gelatin capsule was filled with the result to prepare a capsule formulation.

Preparation Example 4

Preparation of Injectable Liquid Formulation 10 mg of Compound 6a, an appropriate amount of injectable sterilized distilled water, and an appropriate amount of a pH controller were mixed, and then, according to a conventional injectable preparation method, an injectable liquid formulation was prepared including the dosage described above per 1 ample (2 ml).

Preparation Example 5

Preparation of Ointment Formulation 10 mg of Compound 6a, 250 mg of PEG-4000, 650 mg of PEG-400, 10 mg of white vaseline, 1.44 mg of methyl p-hydroxybenzoate, 0.18 mg of propyl p-hydroxybenzoate, and the balance of purified water were mixed, and then, an ointment formulation was prepared according to a conventional ointment preparation method.

It should be understood that the exemplary embodiments described herein should be considered in a descriptive sense only and not for purposes of limitation, and do not limit the scope of the present invention. Accordingly, the substantial scope of the present invention is defined by the following claims and equivalents thereto.

The invention claimed is:

1. A method of treating a lung cancer, comprising:
administering a pharmaceutical composition comprising a 6-aminopyridin-3-ol compound of Formula 1 below or a pharmaceutically acceptable salt thereof as an active ingredient to a subject:

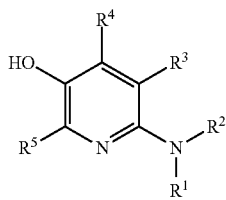

[Formula 1]

wherein
$R^1$ is a hydrogen, a C1 to C4 alkyl, or a phenyl, $R^2$ is a hydrogen, a C1 to C16 alkyl, a C1 to C16 hydroxyalkyl, a C2 to C4 (5-hydroxy-trimethylpyridin-2-yloxy)alkyl, a C3 to C7 cycloalkyl, benzyl, a phenyl, a C1 to C4 alkylphenyl, a nitrophenyl, a halophenyl, a benzo[d][1,3]-dioxol-5-yl, or a pyridine-2-yl; or $R^1$ and $R^2$ are linked to each other to form a 5-membered ring or a 6-membered ring, thereby forming a heterocyclic compound, and are any one selected from pyrrolidine-1-yl, 4-methylpiperazine-1-yl, 6-morpholino, and 1H-pyrrol-1-yl, and
each of $R^3$ to $R^5$ is a methyl.

2. The method according to claim 1, wherein $R^1$ is a hydrogen, a C1 to C4 alkyl, or a phenyl, $R^2$ is a hydrogen, a C6 to C16 alkyl, a C1 to C6 hydroxyalkyl, (5-hydroxy-3,4,6-trimethylpyridin-2-yloxy)propyl, a C5 to C6 cycloalkyl, a benzyl, a phenyl, a C1 to C4 alkylphenyl, a nitrophenyl, a halophenyl, or a benzo[d][1,3]-dioxol-5-yl or pyridine-2-yl; or $R^1$ and $R^2$ are linked to each other to form a 5-membered ring to a 6-membered ring, thereby forming a heterocyclic compound, and are each pyrrolidine-1-yl, 4-methylpiperazine-1-yl, 6-morpholino, or 1H-pyrrol-1-yl, and each of $R^3$ to $R^5$ is a methyl.

3. The method according to claim 1, wherein the pharmaceutically acceptable salt is an acid-added salt from an organic acid selected from the group consisting of an oxalic acid, a maleic acid, a fumaric acid, a malic acid, a tartaric acid, a citric acid, and a benzoic acid.

4. The method according to claim 1, wherein the compound or pharmaceutically acceptable salt thereof is selected from 6-amino-2,4,5-trimethylpyridin-3-ol; 6-(hexylamino)-2,4,5-trimethylpyridin-3-ol; 6-(hexadecylamino)-2,4,5-trimethylpyridin-3-ol; 6-((3-hydroxypropyl)amino)-2,4,5-trimethylpyridin-3-ol; 6-(3-((5-hydroxy-3,4,6-trimethylpyridin-2-yl)amino)propoxy)-2,4,5-trimethylpyridin-3-ol; (6-(cyclohexylamino)-2,4,5-trimethylpyridin-3-ol; 6-(benzylamino)-2,4,5-trimethylpyridin-3-ol; 2,4,5-Trimethyl-6-(phenylamino)pyridin-3-ol; 6-((2-isopropylphenyl)amino)-2,4,5-trimethylpyridin-3-ol; 2,4,5-trimethyl-6-((4-nitrophenyl)amino)pyridin-3-ol; 6-((4-bromophenyl)amino)-2,4,5-trimethylpyridin-3-ol; 2,4,5-trimethyl-6-(phenylamino)pyridin-3-ol hydrobromide; 6-(benzo[d][1,3]dioxol-5-ylamino)-2,4,5-trimethylpyridin-3-ol; 6-(diphenylamino)-2,4,5-trimethylpyridin-3-ol; 2,4,5-trimethyl-6-(pyrrolidin-1-yl)pyridin-3-ol; 2,4,5-trimethyl-6-(4-methylpiperazin-1-yl)pyridin-3-ol; 2,4,5-trimethyl-6-morpholinopyridin-3-ol; 2,4,5-trimethyl-6-(1H-pyrrol-1-yl)pyridin-3-ol; and 2,4,5-trimethyl-6-(methyl(pyridin-2-yl)amino)pyridin-3-ol.

5. The method according to claim 1, wherein the pharmaceutically acceptable salt is an acid-added salt from an inorganic acid selected from the group consisting of a hydrochloric acid, a sulfuric acid, a phosphoric acid, and a hydrobromic acid.

* * * * *